US007517352B2

(12) United States Patent
Evans et al.

(10) Patent No.: US 7,517,352 B2
(45) Date of Patent: Apr. 14, 2009

(54) DEVICES FOR PERCUTANEOUS REMOTE ENDARTERECTOMY

(75) Inventors: Michael Evans, Palo Alto, CA (US); Denise Demarais, San Jose, CA (US); Gwendolyn Watanabe, Sunnyvale, CA (US); Stephen Leeflang, Stanford, CA (US)

(73) Assignee: Bacchus Vascular, Inc., Santa Clara, CA (US)

( * ) Notice: Subject to any disclaimer, the term of this patent is extended or adjusted under 35 U.S.C. 154(b) by 1642 days.

(21) Appl. No.: 09/820,084

(22) Filed: Mar. 27, 2001

(65) Prior Publication Data

US 2002/0029052 A1 Mar. 7, 2002

Related U.S. Application Data

(60) Provisional application No. 60/195,653, filed on Apr. 7, 2000, provisional application No. 60/274,104, filed on Apr. 7, 2001.

(51) Int. Cl.
*A61M 29/00* (2006.01)
(52) U.S. Cl. ....................... 606/192; 606/167
(58) Field of Classification Search ............... 606/159, 606/170, 180, 200, 167; 604/22, 96, 97, 604/98, 99–103; 15/104.03, 104.09
See application file for complete search history.

(56) References Cited

U.S. PATENT DOCUMENTS

| 3,320,957 A | 5/1967 | Sokolik |
| 3,539,034 A | 11/1970 | Tafeen |
| 3,996,938 A | 12/1976 | Clark, III |

(Continued)

FOREIGN PATENT DOCUMENTS

WO      WO 95/11633      5/1995

(Continued)

OTHER PUBLICATIONS

Schmitz-Rode et al., "New Device for Percutaneous Fragmentation of Pulmonary Emboli," *Radiology*, vol. 180, No. 1, pp. 135-137, 1991.

(Continued)

*Primary Examiner*—Justine R Yu
(74) *Attorney, Agent, or Firm*—Townsend and Townsend and Crew LLP

(57) ABSTRACT

The present invention provides devices, systems, methods and kits for the percutaneous removal of unwanted tissue or obstructive matter from body cavities or lumens, particularly from the vasculature. Blood vessels, including the coronary, peripheral and neurovascular circulation, which are narrowed or blocked by atheromatous material or plaque are often treated with traditional endarterectomy procedures. The present invention allows the benefits of such a procedure with an intraluminal approach, particularly a percutaneous approach. Generally, the present invention provides a set of catheters or tools which are percutaneously introduceable to the site of the blockage or occlusion. The tools dissect or cut through the innermost tissue layer of the lumen to an underlying tissue layer. The innermost tissue layer is then stripped away from the underlying layer with the occlusive material thereattached. The detached tissue layer and occlusive material is then removed from the lumen; this may include additional cutting, maceration and removal through mechanical aspiration. In any case, the resulting lumen is free of obstruction.

40 Claims, 19 Drawing Sheets

U.S. PATENT DOCUMENTS

| | | | |
|---|---|---|---|
| 4,404,971 A | 9/1983 | LeVeen et al. |
| 4,445,892 A | 5/1984 | Hussein et al. |
| 4,580,568 A | 4/1986 | Gianturco |
| 4,621,636 A | 11/1986 | Fogarty |
| 4,636,195 A | 1/1987 | Wolinsky |
| 4,646,736 A | 3/1987 | Auth |
| 4,665,906 A | 5/1987 | Jervis |
| 4,705,502 A | 11/1987 | Patel |
| 4,754,752 A | 7/1988 | Ginsburg et al. |
| 4,762,130 A | 8/1988 | Fogarty et al. |
| 4,769,005 A | 9/1988 | Ginsburg et al. |
| 4,781,677 A | 11/1988 | Wilcox |
| 4,790,310 A | 12/1988 | Ginsburg et al. |
| 4,824,436 A | 4/1989 | Wolinsky |
| 4,873,978 A | 10/1989 | Ginsburg |
| 4,886,062 A | 12/1989 | Wiktor |
| 4,887,613 A | 12/1989 | Farr et al. |
| 4,895,166 A | 1/1990 | Farr et al. |
| 4,911,163 A | 3/1990 | Fina |
| 4,926,858 A | 5/1990 | Gifford, III et al. |
| 4,966,604 A | 10/1990 | Reiss |
| 5,011,488 A | 4/1991 | Ginsburg |
| 5,014,421 A | 5/1991 | Swarden et al. |
| 5,019,088 A | 5/1991 | Farr |
| 5,041,093 A | 8/1991 | Chu |
| 5,067,957 A | 11/1991 | Jervis |
| 5,090,960 A | 2/1992 | Don Michael |
| 5,116,352 A | 5/1992 | Schnepp-Pesch et al. |
| 5,133,732 A | 7/1992 | Wiktor |
| 5,163,905 A | 11/1992 | Don Michael |
| 5,167,627 A | 12/1992 | Clegg et al. |
| 5,176,638 A | 1/1993 | Don Michael |
| 5,176,693 A | 1/1993 | Pannek, Jr. |
| 5,195,955 A | 3/1993 | Don Michael |
| 5,215,105 A | 6/1993 | Kizelshteyn et al. |
| 5,222,941 A | 6/1993 | Don Michael |
| 5,224,945 A | 7/1993 | Pannek, Jr. |
| 5,226,909 A | 7/1993 | Evans et al. |
| 5,246,014 A | 9/1993 | Williams et al. |
| 5,287,861 A | 2/1994 | Wilk |
| 5,312,341 A | 5/1994 | Turi |
| 5,312,360 A | 5/1994 | Behl |
| 5,312,425 A | 5/1994 | Evans et al. |
| 5,322,513 A | 6/1994 | Walker |
| 5,328,470 A | 7/1994 | Nabel et al. |
| 5,330,484 A | 7/1994 | Günther et al. |
| 5,334,211 A | 8/1994 | Shiber |
| 5,342,306 A | 8/1994 | Don Michael |
| 5,356,418 A | 10/1994 | Shturman |
| 5,380,284 A | 1/1995 | Don Michael |
| 5,387,193 A | 2/1995 | Miraki |
| 5,409,019 A | 4/1995 | Wilk |
| 5,413,581 A | 5/1995 | Goy |
| 5,419,774 A | 5/1995 | Willard et al. |
| 5,423,799 A | 6/1995 | Shiu |
| 5,429,144 A | 7/1995 | Wilk |
| 5,439,447 A | 8/1995 | Miraki |
| 5,443,497 A | 8/1995 | Venbrux |
| 5,454,790 A | 10/1995 | Dubrul |
| 5,460,610 A | 10/1995 | Don Michael |
| 5,462,529 A | 10/1995 | Simpson et al. |
| 5,464,395 A | 11/1995 | Faxon et al. |
| 5,501,694 A | 3/1996 | Ressemann et al. |
| 5,540,707 A | 7/1996 | Ressemann et al. |
| 5,556,408 A | 9/1996 | Farhat |
| 5,569,275 A | 10/1996 | Kotula et al. |
| 5,569,277 A | 10/1996 | Evans et al. |
| 5,569,295 A | 10/1996 | Lam |
| 5,571,122 A | 11/1996 | Kelly et al. |
| 5,571,130 A | 11/1996 | Simpson et al. |
| 5,584,803 A | 12/1996 | Stevens et al. |
| 5,597,378 A | 1/1997 | Jervis |
| 5,616,149 A | 4/1997 | Barath |
| 5,643,199 A | 7/1997 | Rowland et al. |
| 5,649,952 A | 7/1997 | Lam |
| 5,681,335 A | 10/1997 | Serra et al. |
| 5,695,507 A | 12/1997 | Auth et al. |
| 5,697,944 A * | 12/1997 | Lary ............................ 606/159 |
| 5,702,368 A | 12/1997 | Stevens et al. |
| 5,728,123 A * | 3/1998 | Lemelson et al. ............. 604/22 |
| 5,742,019 A | 4/1998 | Radisch, Jr. |
| 5,766,191 A | 6/1998 | Trerotola |
| 5,769,812 A | 6/1998 | Stevens et al. |
| 5,795,322 A | 8/1998 | Boudewijn |
| 5,814,058 A | 9/1998 | Carlson et al. |
| 5,824,040 A | 10/1998 | Cox et al. |
| 5,830,125 A | 11/1998 | Scribner et al. |
| 5,833,644 A | 11/1998 | Zadno-Azizi et al. |
| 5,836,905 A | 11/1998 | Lemelson et al. |
| 5,843,102 A | 12/1998 | Kalmann et al. |
| 5,857,999 A | 1/1999 | Quick et al. |
| 5,873,882 A | 2/1999 | Straub et al. |
| 5,876,414 A | 3/1999 | Straub |
| 5,879,361 A | 3/1999 | Nash |
| 5,885,238 A | 3/1999 | Stevens et al. |
| 5,899,909 A | 5/1999 | Claren et al. |
| 5,902,316 A | 5/1999 | Mollenauer |
| 5,904,698 A | 5/1999 | Thomas et al. |
| 5,916,193 A | 6/1999 | Stevens et al. |
| 5,916,234 A | 6/1999 | Lam |
| 5,928,186 A | 7/1999 | Homsma et al. |
| 5,947,985 A | 9/1999 | Imran |
| 5,954,713 A | 9/1999 | Newman et al. |
| 5,954,737 A | 9/1999 | Lee |
| 5,972,019 A | 10/1999 | Engelson et al. |
| 6,001,112 A | 12/1999 | Taylor |
| 6,036,708 A | 3/2000 | Sciver |
| 6,066,149 A * | 5/2000 | Samson et al. ............... 606/159 |
| 6,066,158 A | 5/2000 | Engelson et al. |
| 6,090,118 A | 7/2000 | McGuckin, Jr. |
| 6,096,054 A * | 8/2000 | Wyzgala et al. .............. 606/170 |
| 6,565,588 B1 * | 5/2003 | Clement et al. .............. 606/180 |
| 2002/0082592 A1 * | 6/2002 | Lary ............................ 606/15 |

FOREIGN PATENT DOCUMENTS

| | | |
|---|---|---|
| WO | WO 96/01591 | 1/1996 |
| WO | WO 97/13463 | 4/1997 |
| WO | WO 97/13471 | 4/1997 |
| WO | WO 98/38929 A1 | 9/1998 |
| WO | WO 99/16362 A1 | 4/1999 |
| WO | WO 99/44510 | 9/1999 |
| WO | WO 99/44542 | 9/1999 |
| WO | WO 00/13651 A1 | 3/2000 |
| WO | WO 00/41762 | 7/2000 |

OTHER PUBLICATIONS

Sharafuddin et al., "Current Status of Percutaneous Mechanical Thrombectomy. Part I. General Principles," *Journal of Vascular and Interventional Radiology*, vol. 8, No. 6, (Nov.-Dec. 1997), pp. 911-921.

* cited by examiner

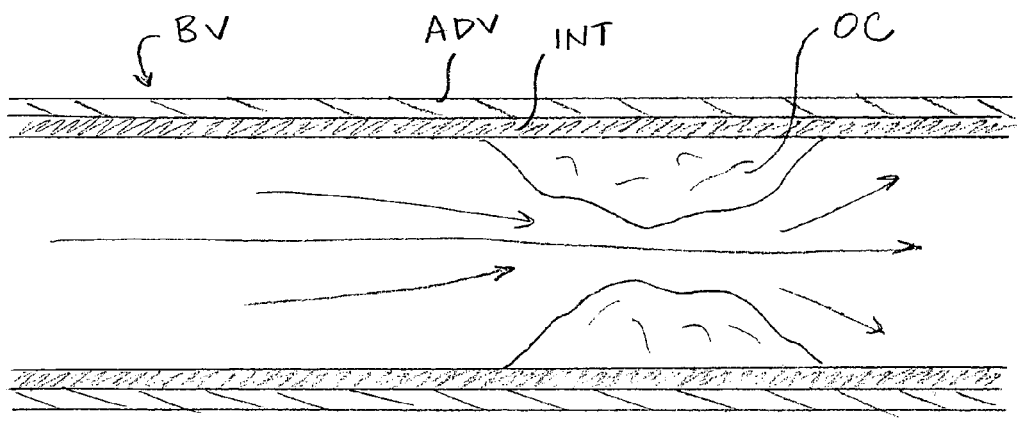
FIG_1A
(PRIOR ART)
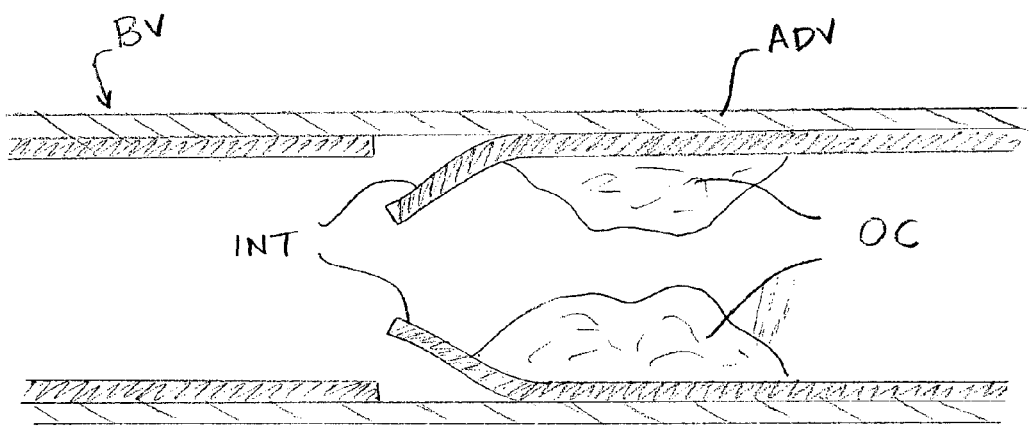
FIG_1B
(PRIOR ART)
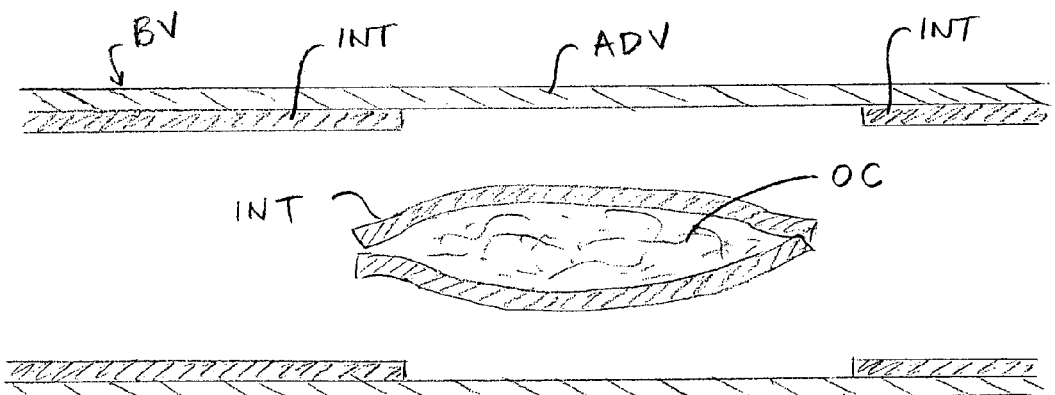
FIG_1C
(PRIOR ART)

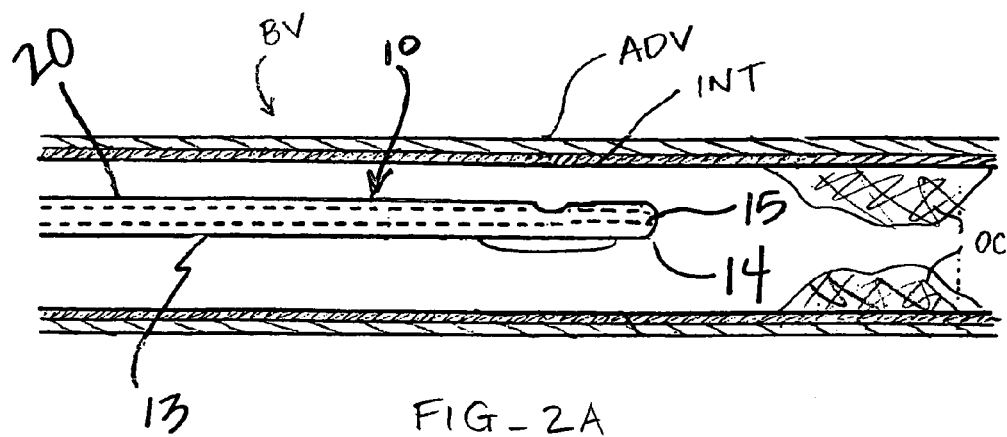
FIG_2A
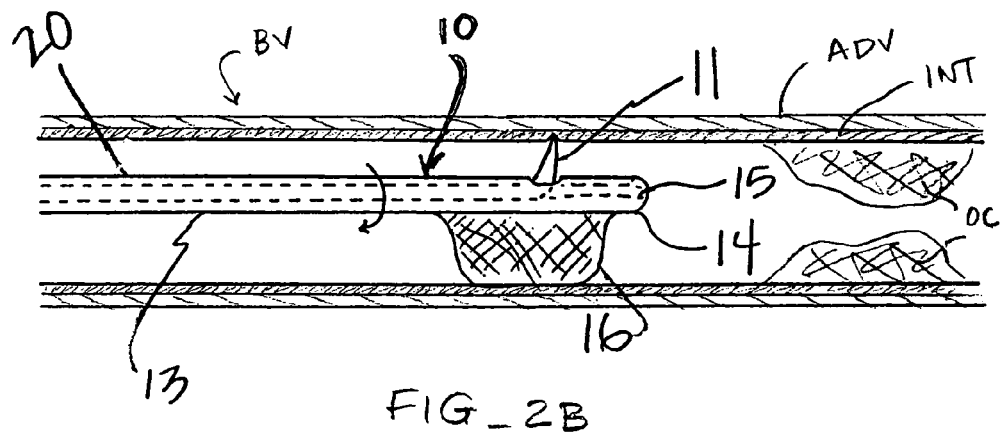
FIG_2B
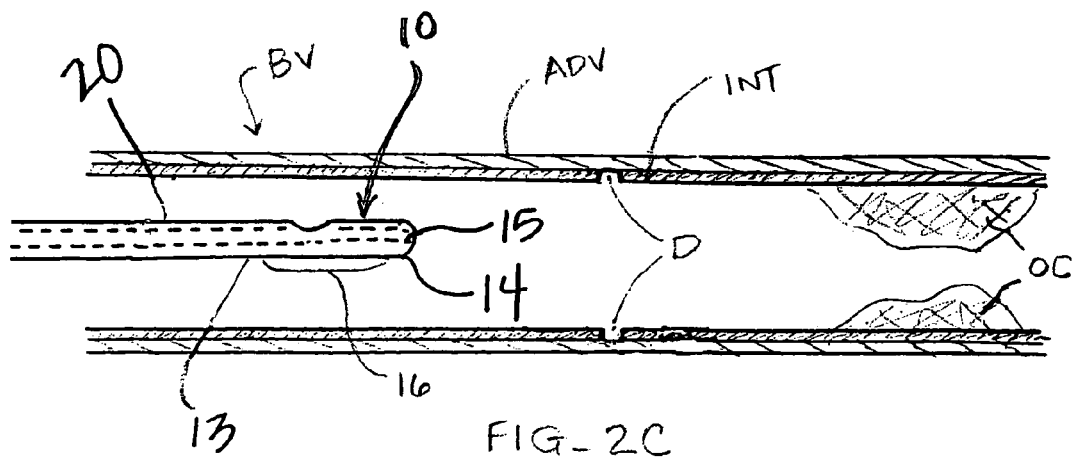
FIG_2C

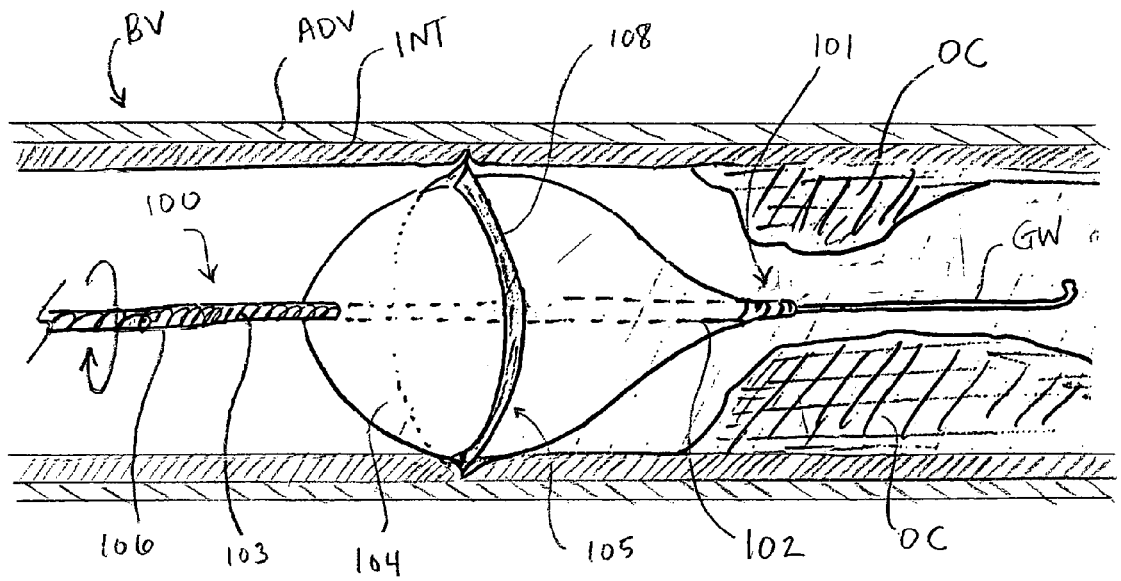
FIG_3A
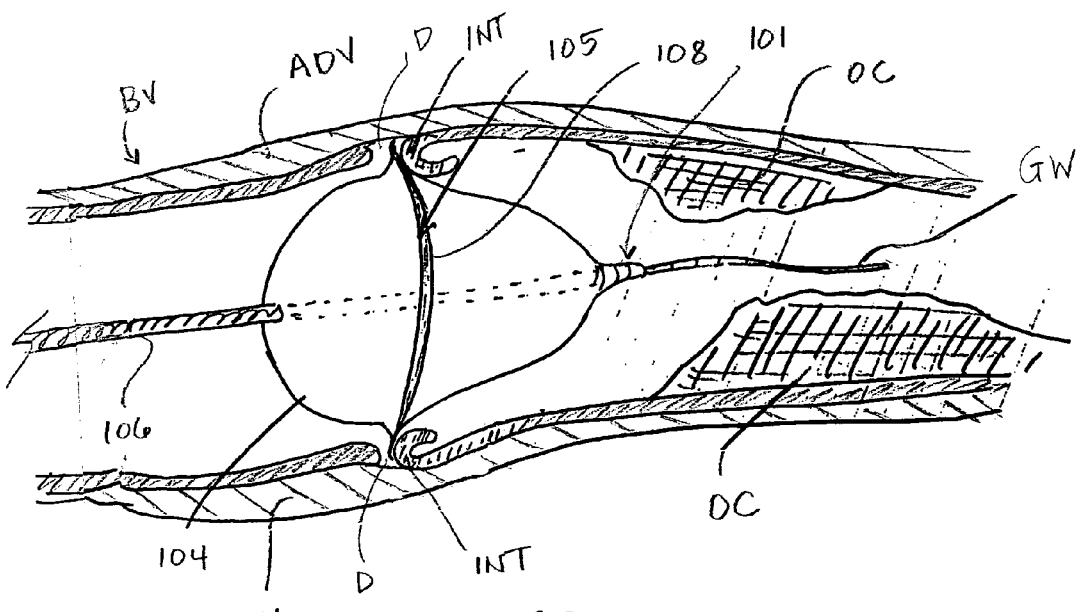
FIG_3B

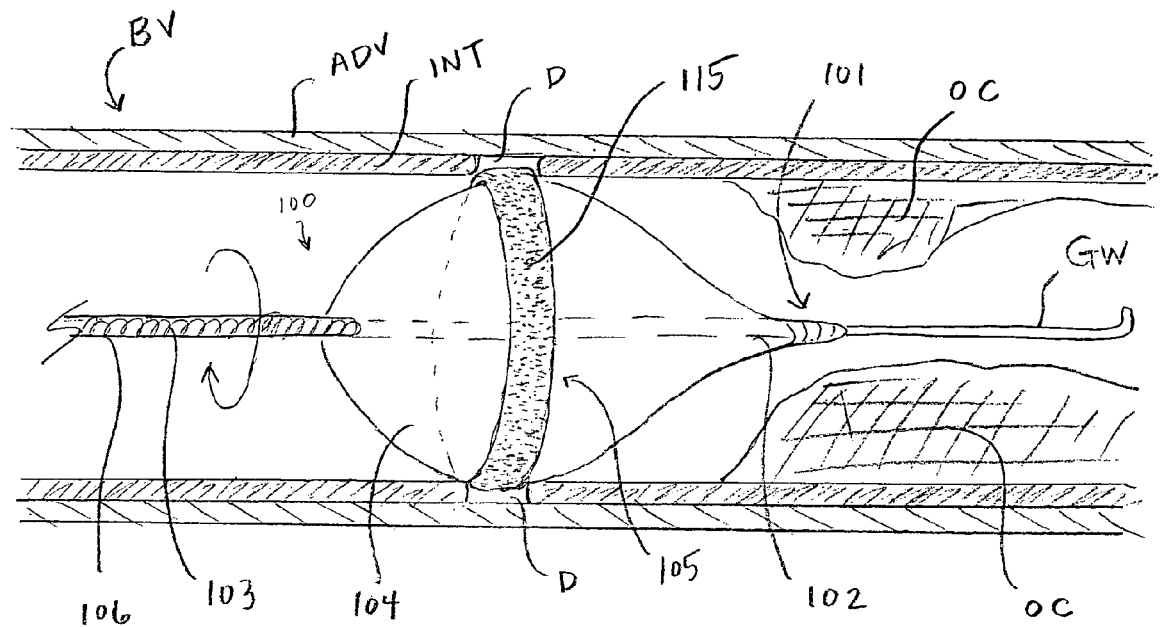
FIG_4
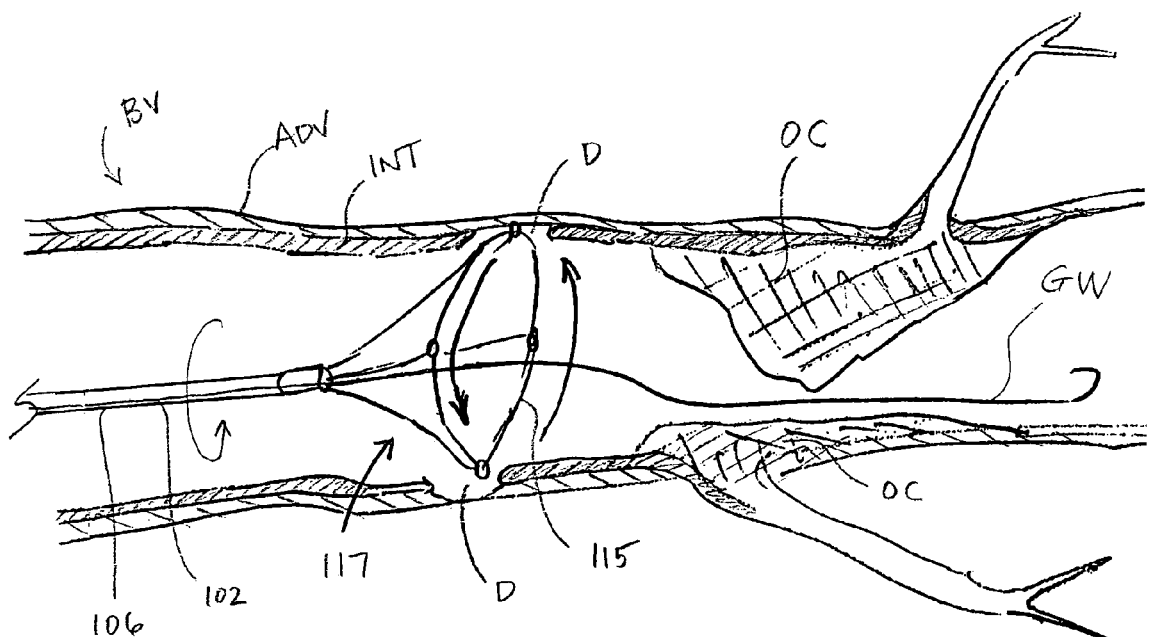
FIG_5

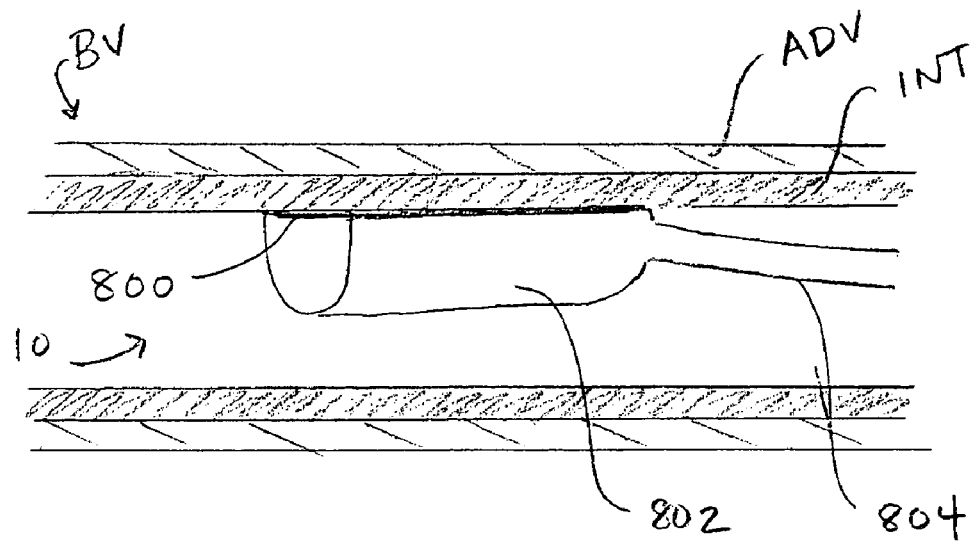
FIG_7A
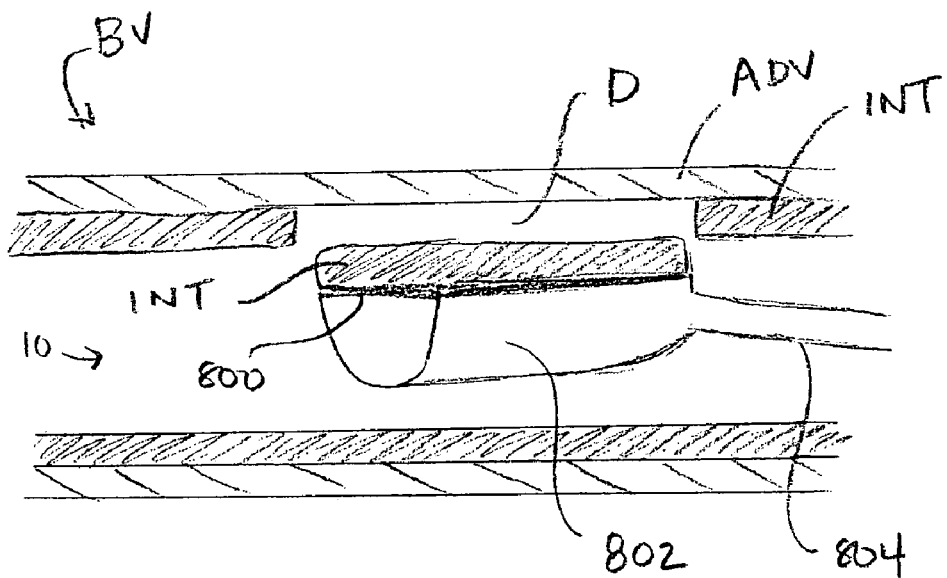
FIG_7B

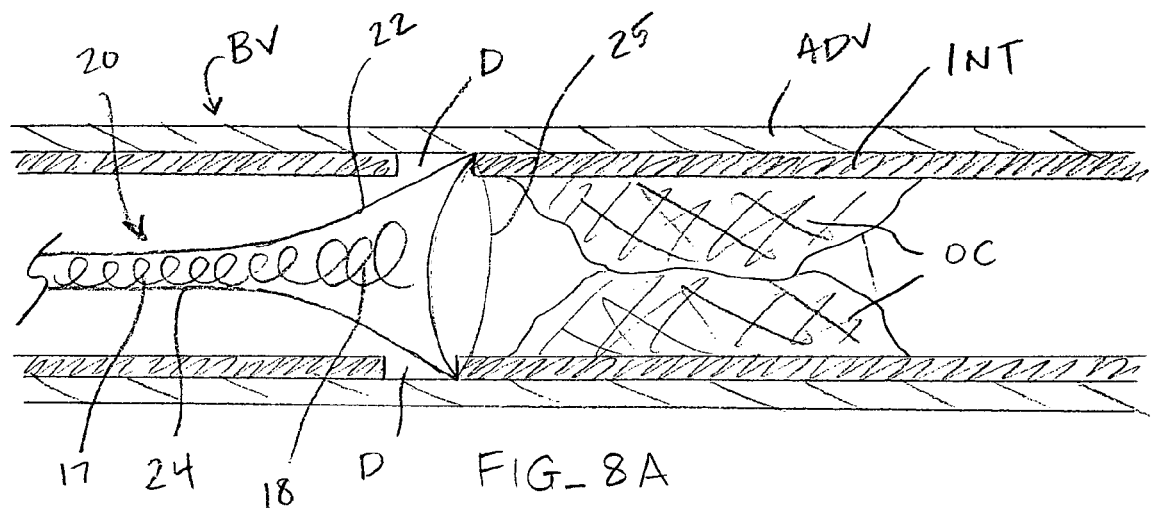
FIG_8A
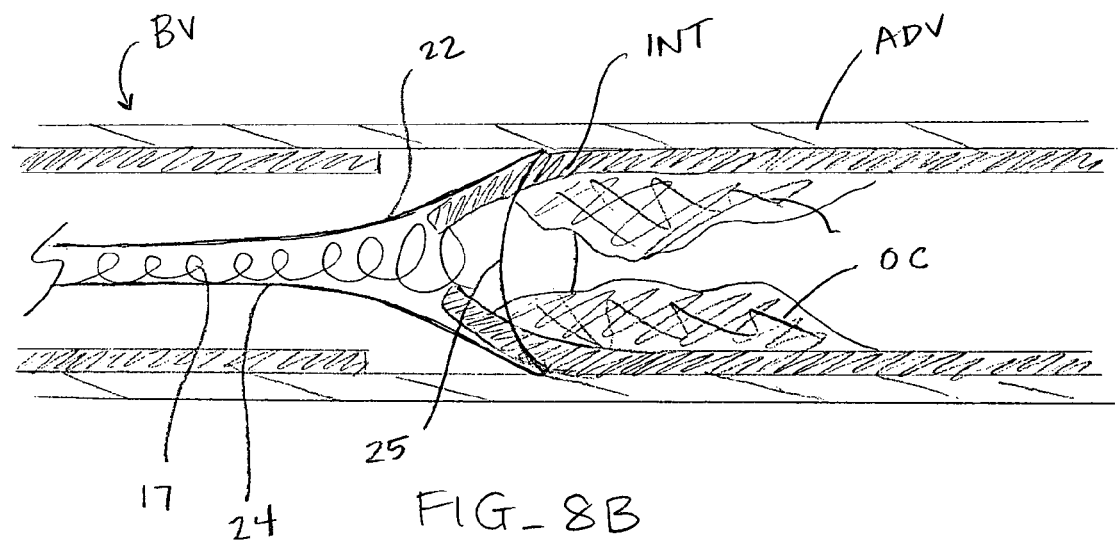
FIG_8B

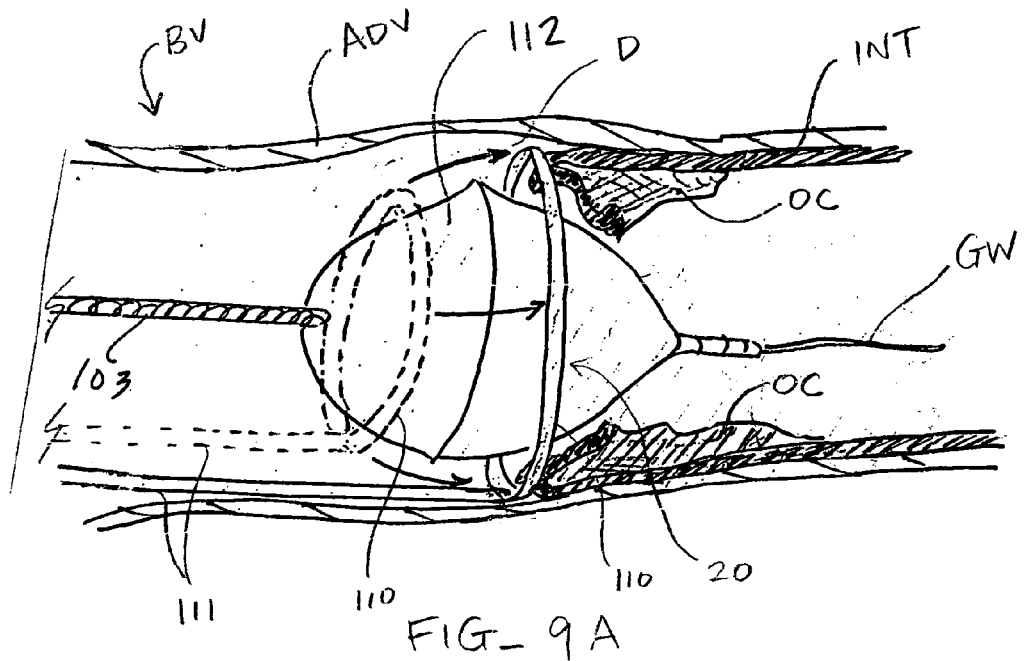
FIG_9A
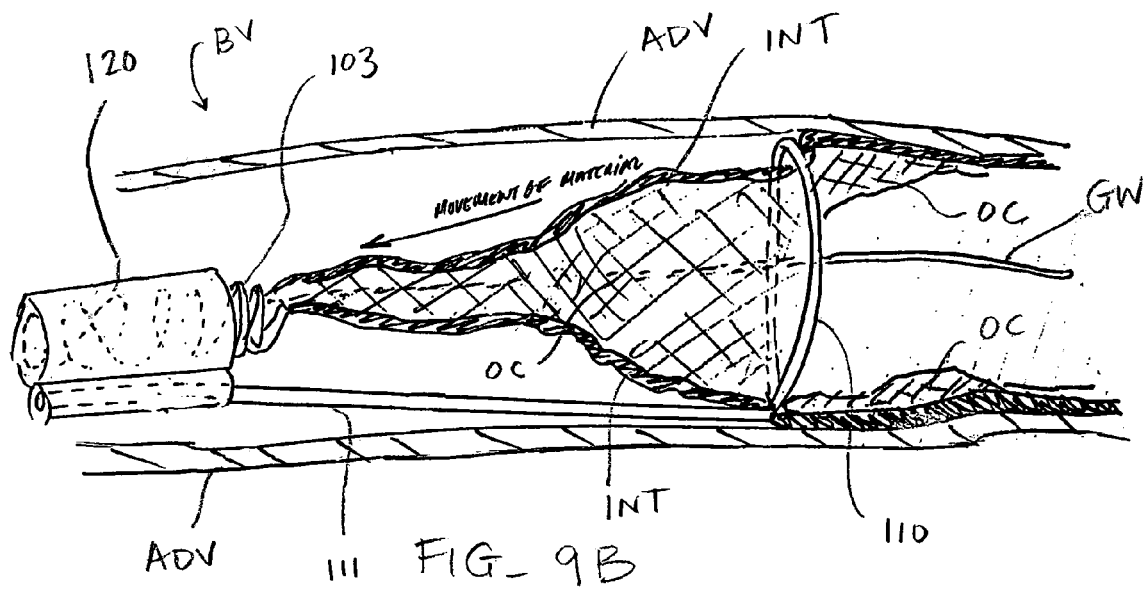
FIG_9B

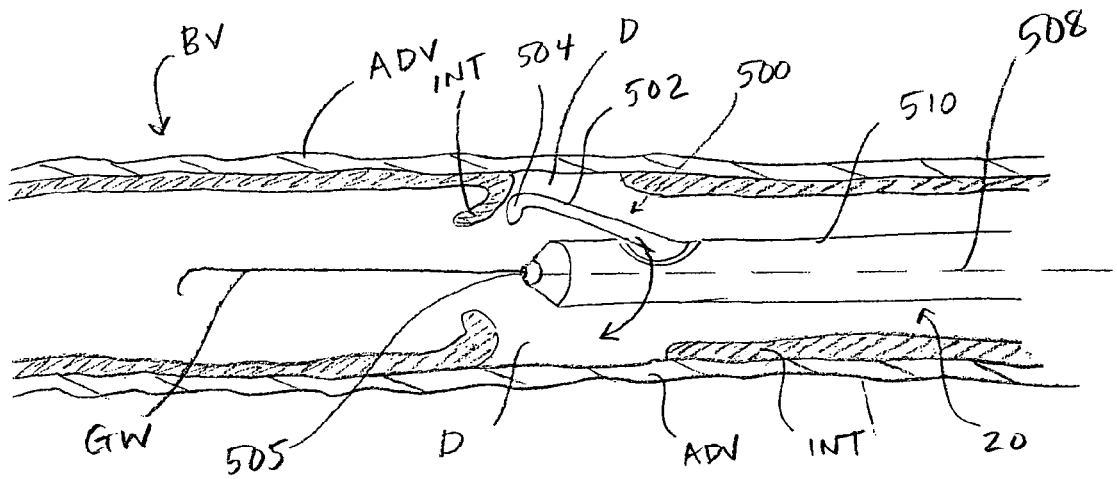
FIG_11
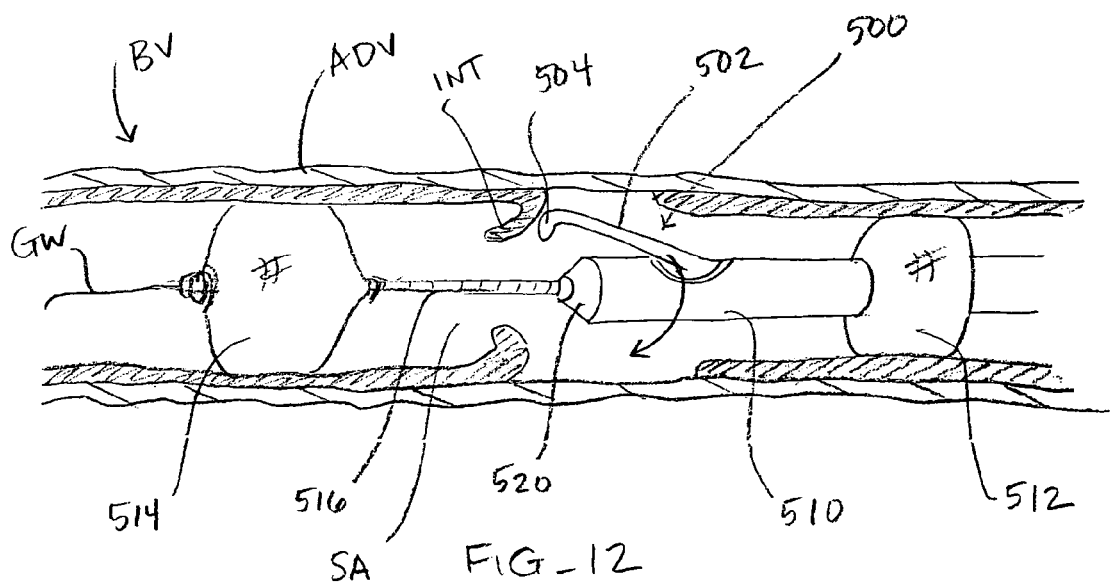
FIG_12

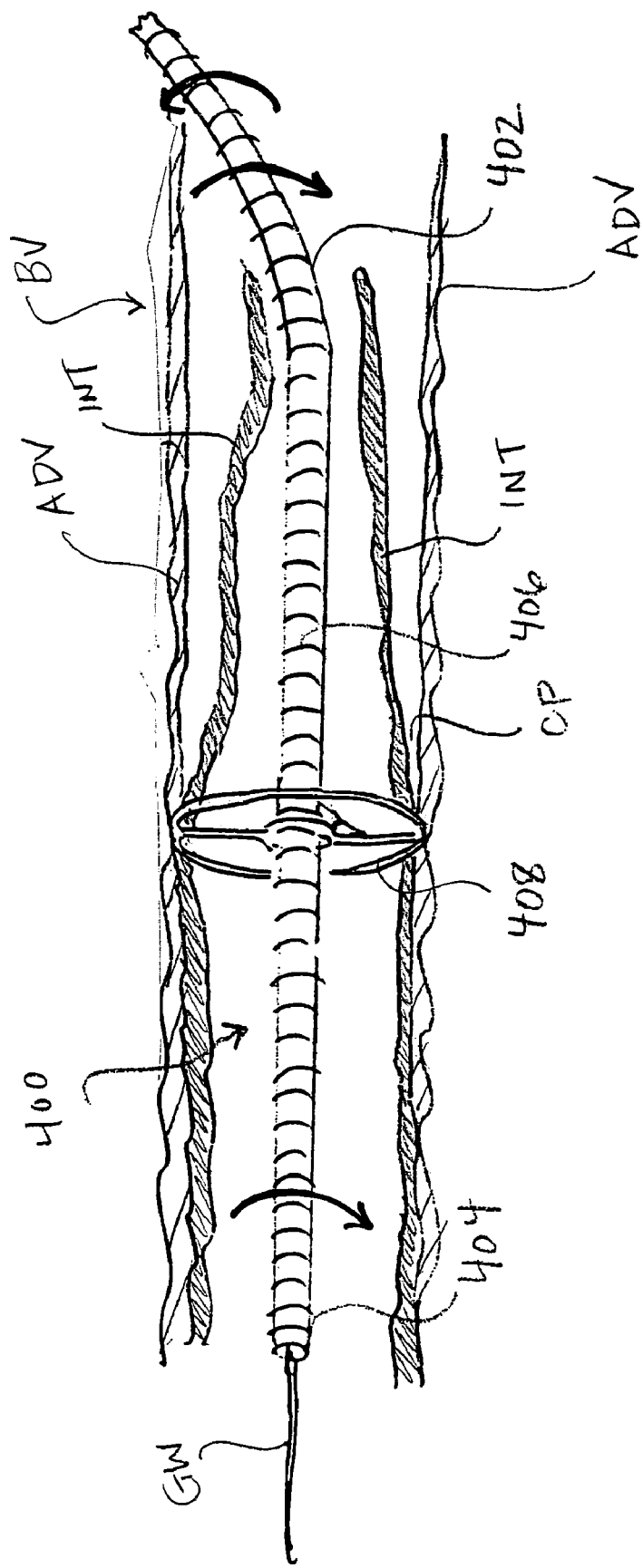
FIG_13

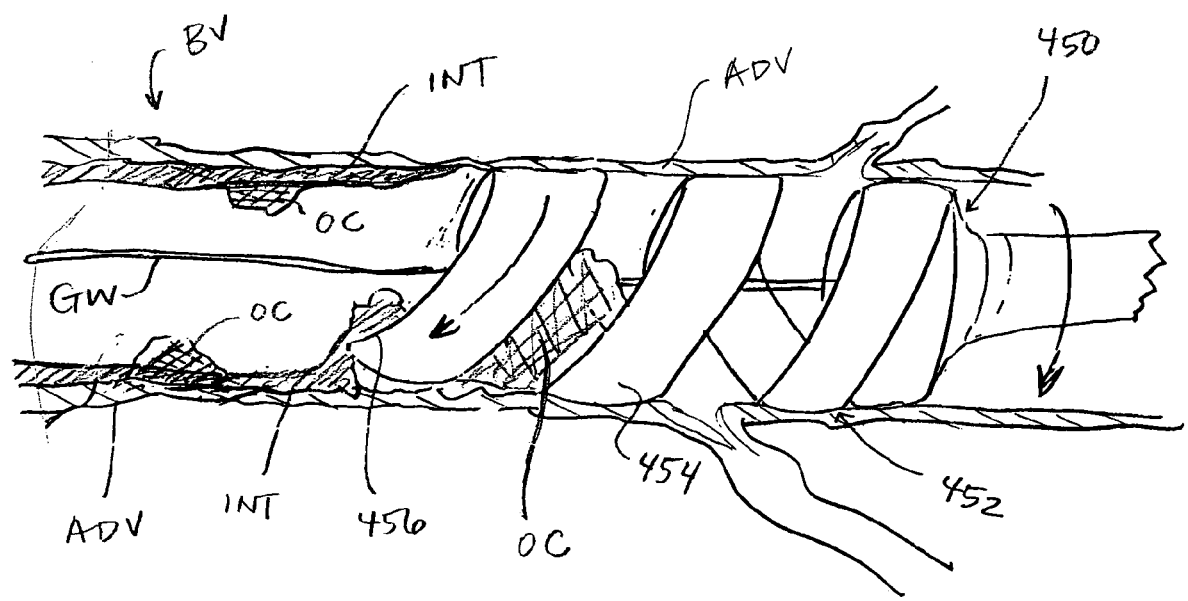
FIG_14

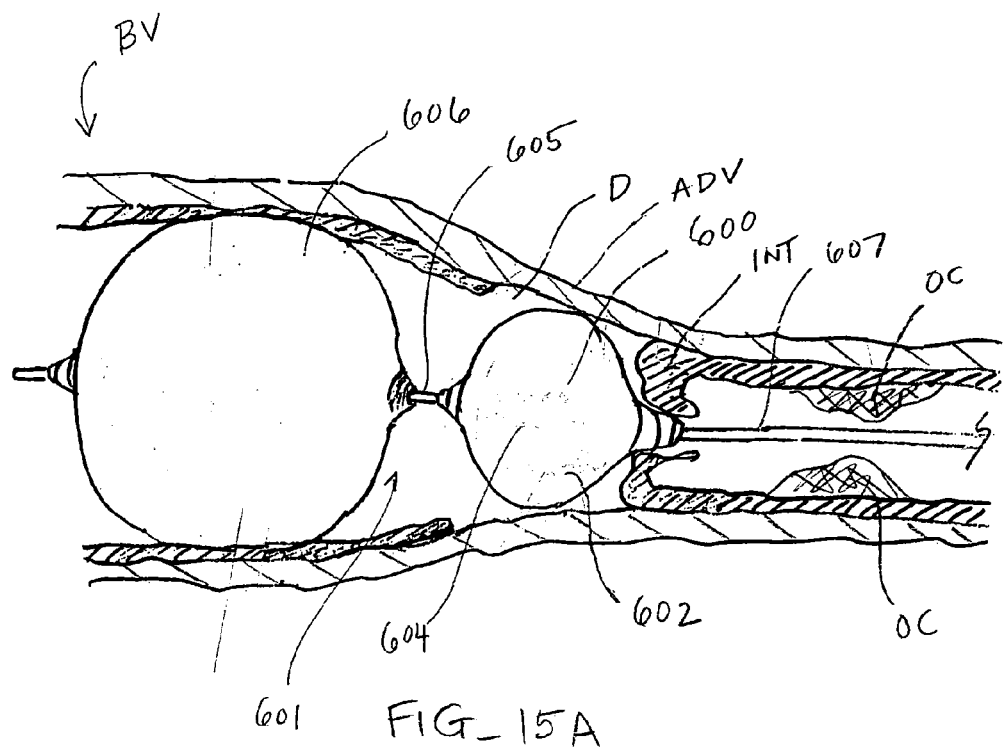
FIG_15A
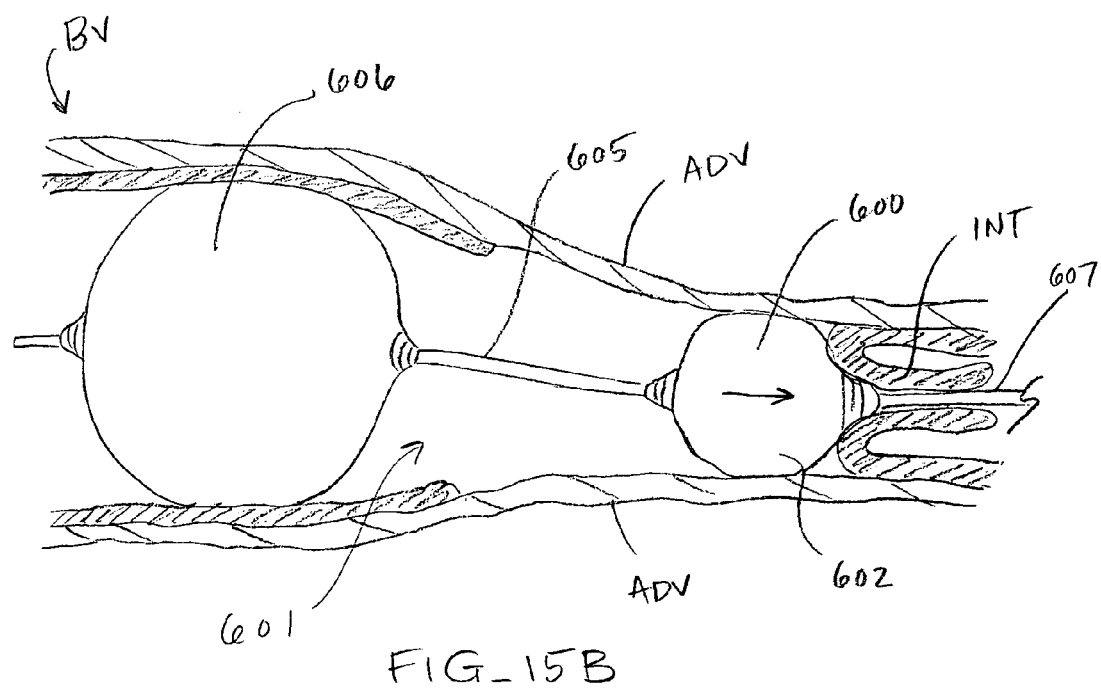
FIG_15B

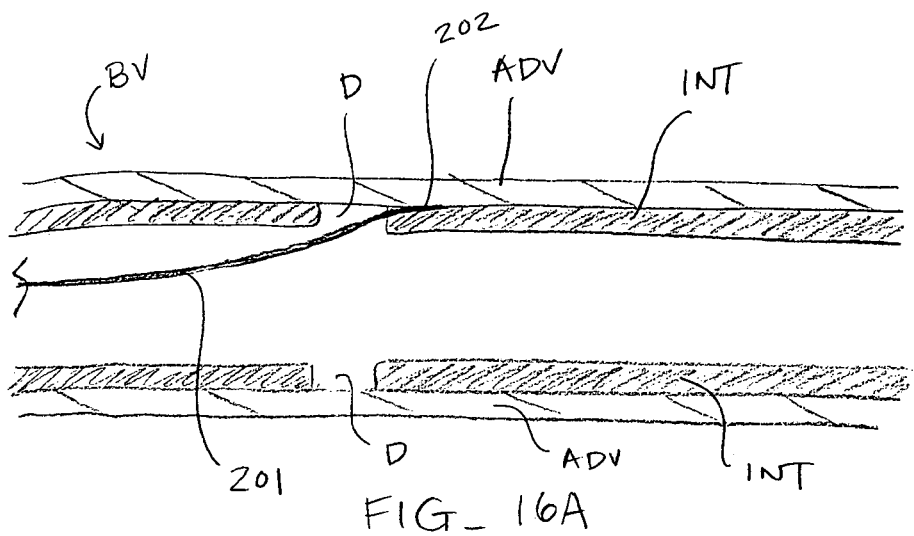
FIG_16A
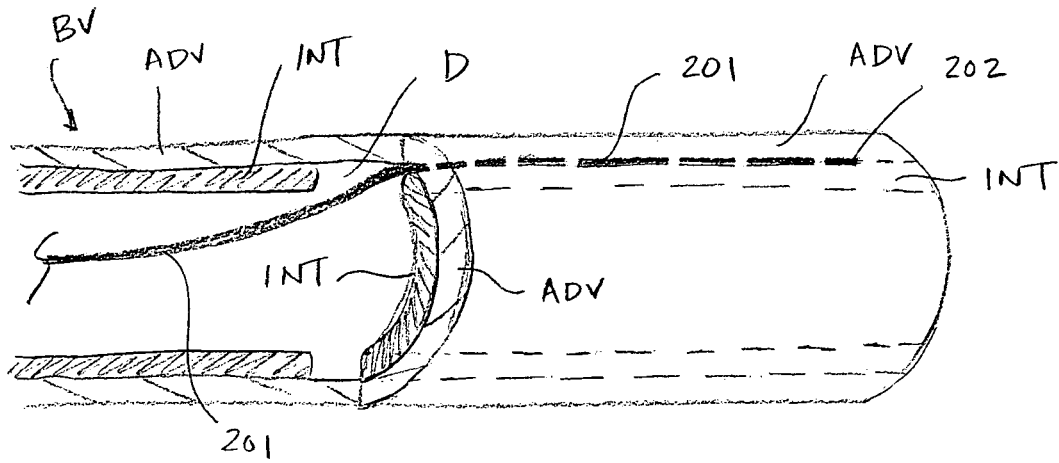
FIG_16B
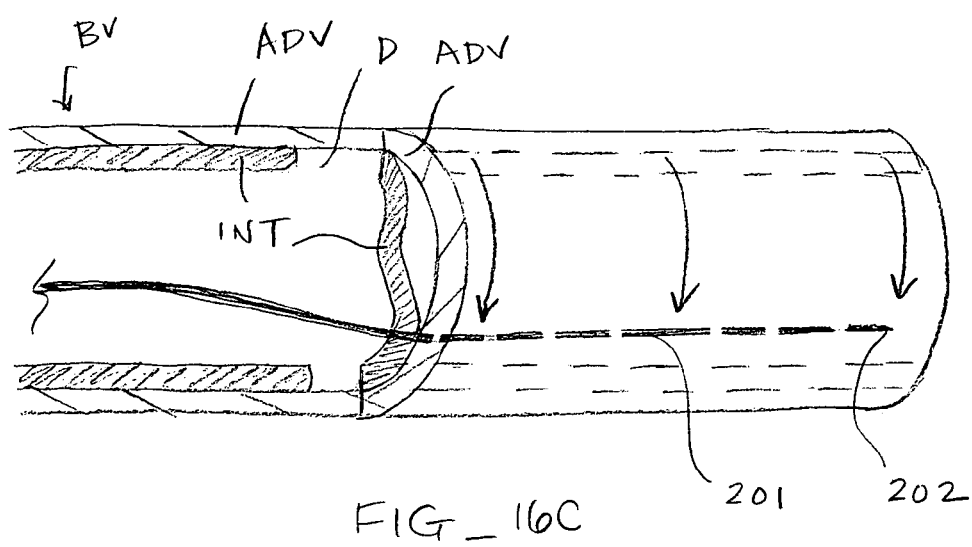
FIG_16C

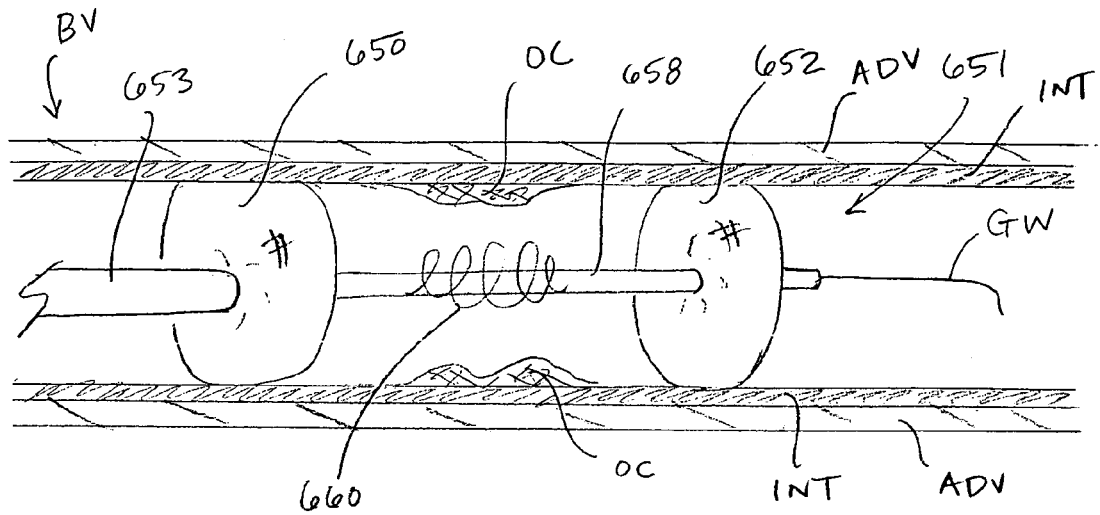
FIG_17A
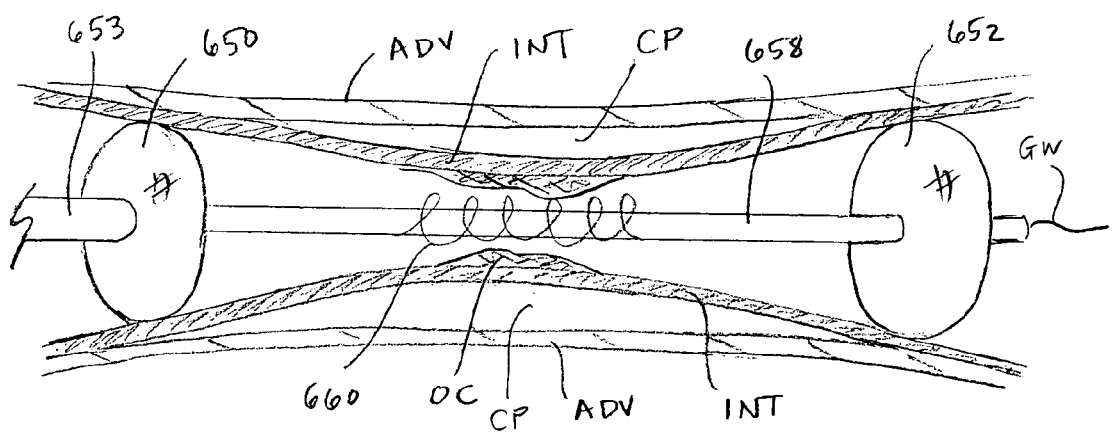
FIG_17B
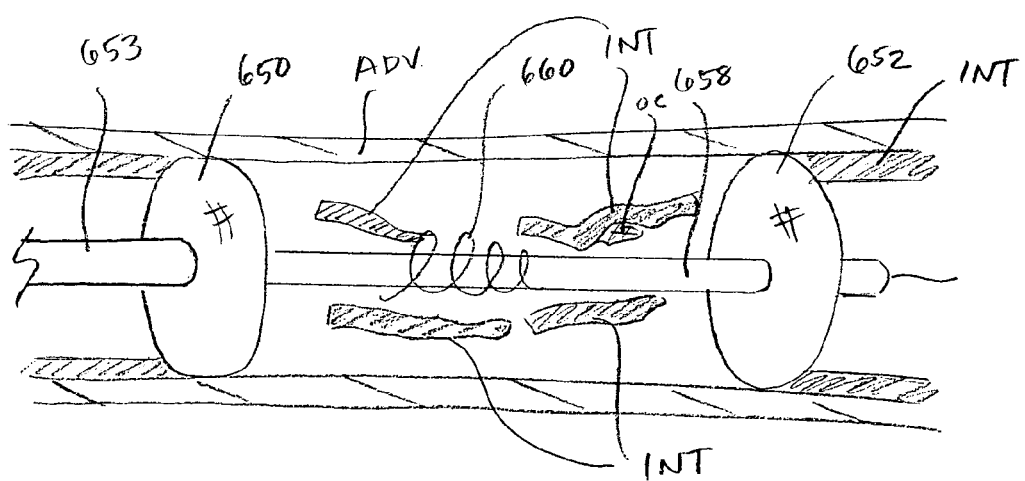
FIG_17C

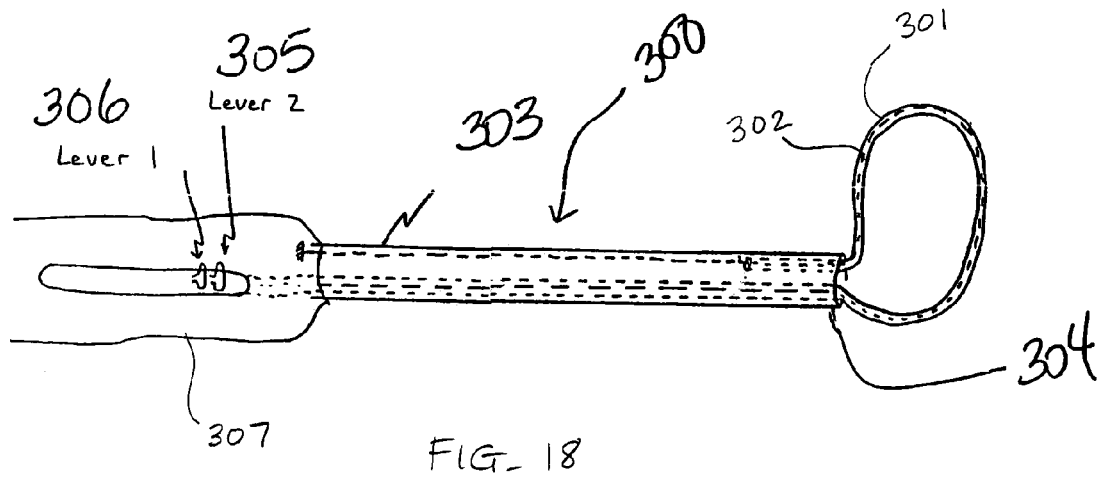
FIG_18
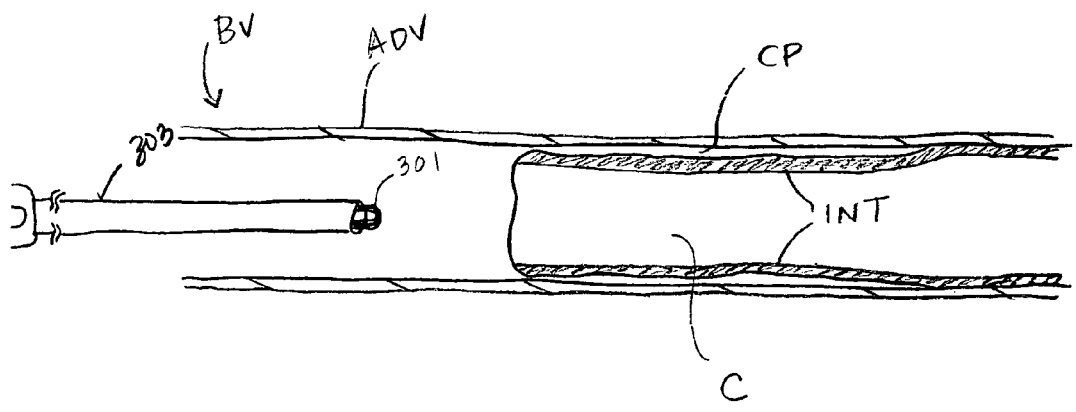
FIG_19A
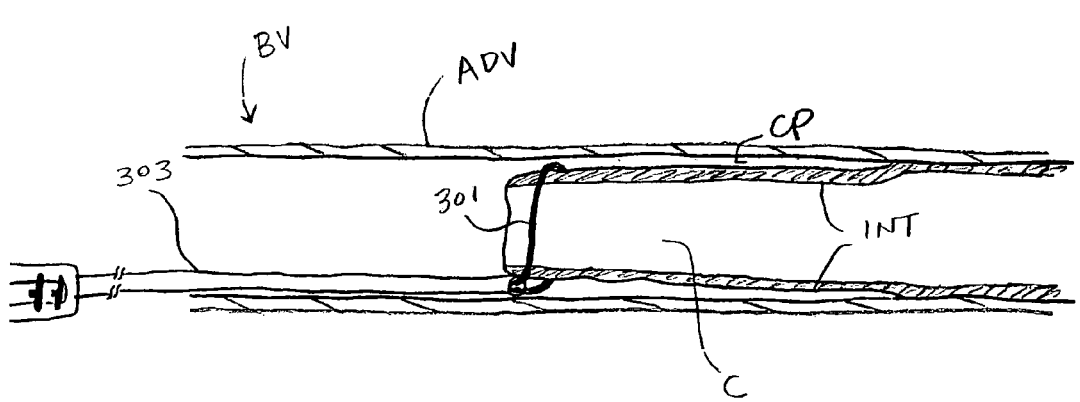
FIG_19B

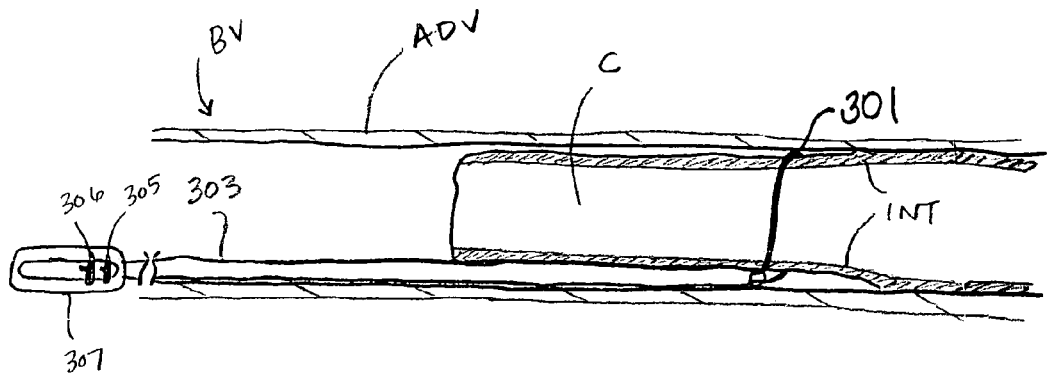
FIG_19C
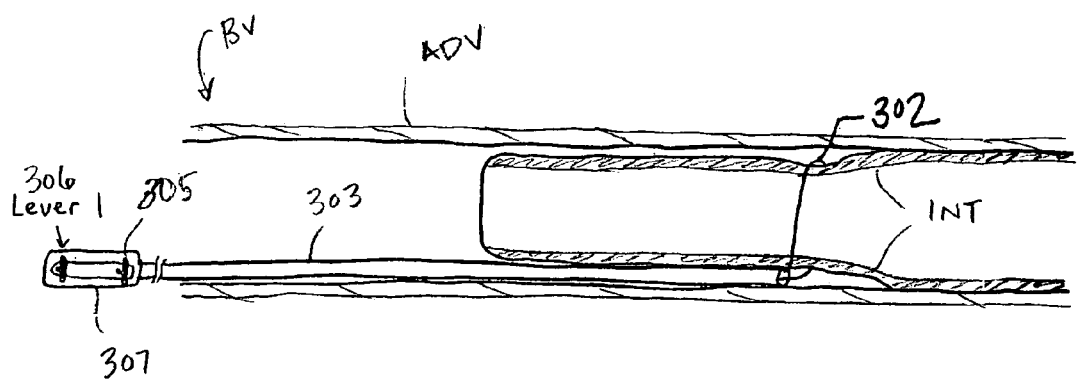
FIG_19D
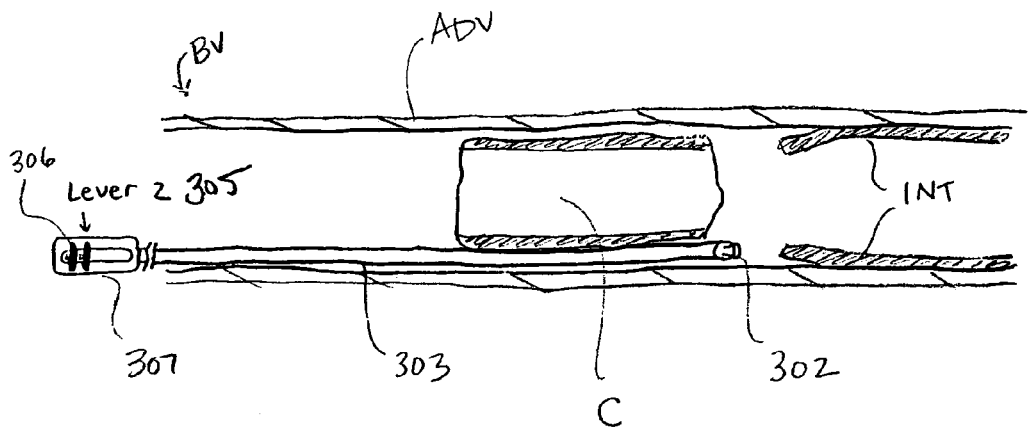
FIG_19E

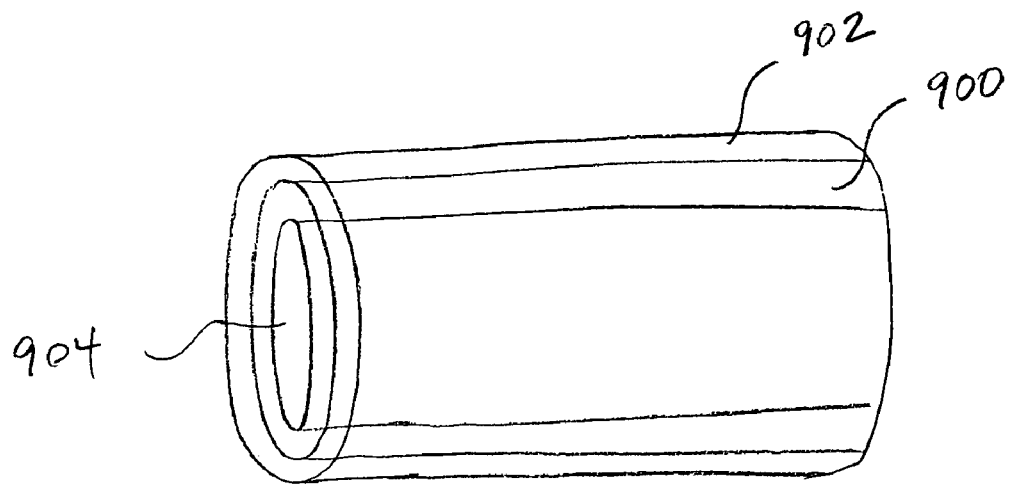
FIG_20A
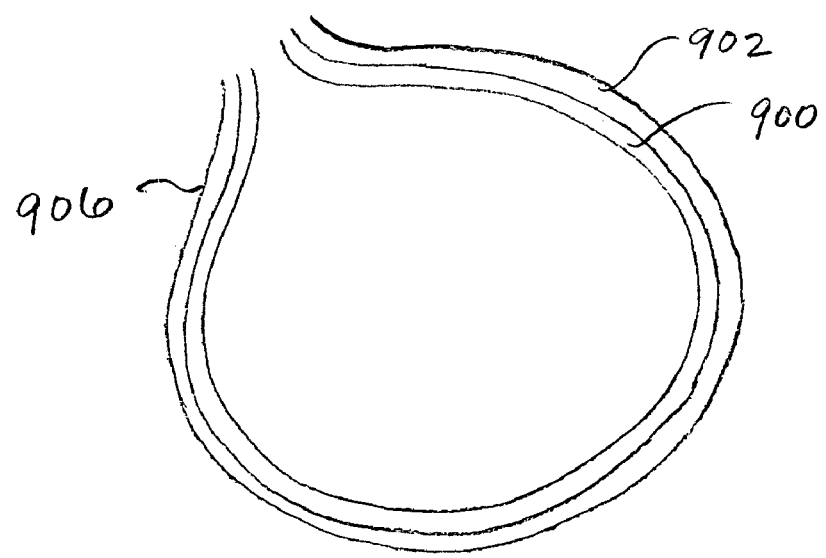
FIG_20B

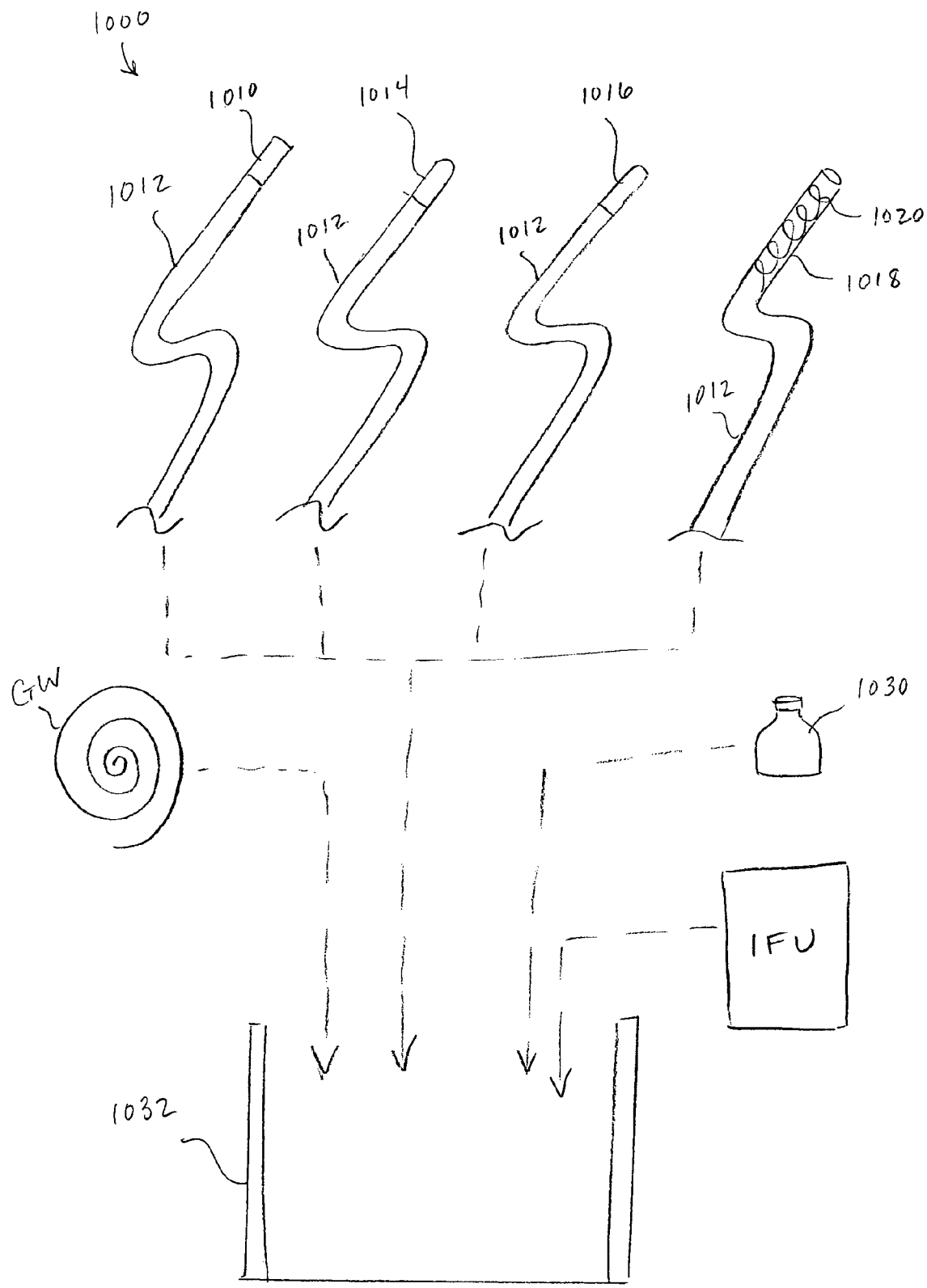
FIG_21

DEVICES FOR PERCUTANEOUS REMOTE ENDARTERECTOMY

CROSS-REFERENCES TO RELATED APPLICATIONS

This application claims the benefit and priority of U.S. Provisional Patent Application No. 60/195,653, filed Apr. 7, 2000, and U.S. Provisional Patent Application No. 60/274104, filed Mar. 7, 2001, the full disclosures of which is hereby incorporated by reference for all purposes.

BACKGROUND OF THE INVENTION

The present invention relates generally to medical apparatus and methods, and more particularly, to devices and methods for percutaneous removal of unwanted tissue such as thrombus, atheroma, fluid, polyps, cysts or other obstructive matter from body lumens, such as blood vessels, ureters, bile ducts or fallopian tubes. More specifically, the present invention relates to the excision of the thickened atheromatous tunica intima of an artery, a procedure known as an endarterectomy.

An endarterectomy is a surgical procedure that removes material involved in a narrowing or blockage of an artery. Typically, such a procedure is performed on the carotid arteries where atheromatous material or plaque has narrowed or occluded the carotid arteries reducing the supply of blood flow to the brain. Untreated, this may lead to neurological deficits and stroke. Deficits can occur due to a decrease in oxygen-rich blood to the brain causing destruction of brain tissue. Strokes can occur due to uncontrolled blood pressure or bursting of weakened blood vessels in the brain. The risk of both of these conditions can be reduced by carotid endarterectomy.

A typical endarterectomy procedure is illustrated in FIGS. 1A-1C. FIG. 1A is a cross-sectional view of a blood vessel BV prior to treatment. As shown, the wall of the blood vessel BV is comprised of two layers, an intimal layer INT or innermost layer of the lumen which is in contact with the blood and an adventitial layer ADV or outer layer which is covered by the intimal layer INT. In this case, the blood vessel BV is narrowed or partially blocked by occlusive material or an occlusion OC. Blood flowing through the vessel is restricted through the area of the occlusion OC as illustrated by arrows. It should be noted that the term occlusion OC might refer to any substance or anatomic morphology that acts to severely occlude a body conduit such that it is difficult to pass a wire from proximal end of the occlusion to the distal end. Depending on the type of material occluding the body conduit (soft plaque, calcified plaque, thrombus, fibrin, clot, fatty tissue etc.) some occlusions may be more severe than others but all are included in the scope of the present invention when there may be some difficulty passing a guidewire therethrough.

Referring to FIG. 1B, an endarterectomy procedure may involve removing the occlusion OC along with the intimal layer INT in the region of the occlusion. Here, the intimal layer INT is cut, split or cleaved to access the adventitial layer ADV. The intimal layer INT is then pulled away, stripped or delaminated from the adventitial layer ADV along the length of the occlusion OC. Referring to FIG. 1C, the intimal layer INT is also cleaved on the opposite side of the occlusion OC to remove the delaminated intimal layer INT containing the occlusion OC from the vessel wall. The excised material may then be removed from the blood vessel BV. It may be appreciated that the above described procedure may be readily adapted for use in any body lumen or body cavity wherein unwanted material may be removed in a similar fashion.

Currently, there are many clinical approaches to removing unwanted material, many of which are performed surgically, wherein the treatment site is accessed directly through a surgical incision. An example of this surgical procedure utilizes a set of surgical tools, like The MollRing Cutter™, which enable the surgeon to cleave a plane of an occluded vessel and strip the atheromatous intimal layer, such as described in U.S. Pat. Nos. 5,843,102 and 5,954,713.

In recent years, a variety of catheter devices have been developed for use in intraluminal and intravascular procedures for fragmentation and removal of blood clots, or thrombus, from blood vessels. More recently, devices that can be inserted percutaneously through a puncture in the skin have been developed to make the procedures less invasive. For example, a catheter device is inserted into a blood vessel at some distance away from the intended treatment site, and is then advanced through the vessel lumen until the selected location is reached. In many cases the vessel to be treated is totally blocked by an occlusive lesion usually comprising, thrombus, soft plaque, and calcified plaque.

Several techniques have been introduced to fragment the unwanted plaque or tissue from blood vessels such as rotating baskets or impellers as described in U.S. Pat. Nos. 5,766,191 and 5,569,275, cutters U.S. Pat. No. 5,501,694, or high pressure fluid infusion to create a Venturi effect as described in U.S. Pat. No. 5,795,322. Other devices, such as atherectomy cutters, may also be employed such as those described in U.S. Pat. Nos. 5,904,968, 5,224,945, 5,312,425 and 5,330,484.

In many instances, these techniques further include aspirating the unwanted occlusive materials through a lumen of the treatment device or using a secondary catheter hooked up to a source of vacuum/suction. Critical to the success of an improved procedure is having a device that can rapidly aspirate the occlusive material from the body lumen. One such device is described in U.S. patent application Ser. No. 09/454,517 and in U.S. Provisional Application No. 60/154,752.

Although these techniques provide many benefits, it is also desired to provide some of the benefits of traditional endarterectomy in intraluminal and intravascular procedures. In particular, it would be desired to percutaneously treat a total occlusion using a set of tools that perform similar functions to those performed in traditional surgical endarterectomy procedures. These tools would first provide a cleavage plane circumferentially or longitudinally of the lesion, dissect the cylindrical core, macerate the core, and aspirate the material. Thus, it would be desirable to provides devices, systems, methods and kits to this end. At least some of these objectives will be met by the aspects of the present invention.

BRIEF SUMMARY OF THE INVENTION

The present invention provides devices, systems, methods and kits for the percutaneous removal of unwanted tissue or obstructive matter from body cavities or lumens, particularly from the vasculature. Blood vessels, including the coronary, peripheral and neurovascular circulation, which are narrowed or blocked by atheromatous material or plaque are often treated with traditional endarterectomy procedures. The present invention allows the benefits of such a procedure with an intraluminal approach, particularly a percutaneous approach. Generally, the present invention provides a set of catheters or tools which are percutaneously introduceable to the site of the blockage or occlusion. The tools dissect or cut through the innermost tissue layer of the lumen to an underlying tissue layer. The innermost tissue layer is then stripped away from the underlying layer with the occlusive material thereattached. The detached tissue layer and occlusive material is then removed from the lumen; this may include additional cutting, maceration and removal through mechanical aspiration. In any case, the resulting lumen is free of obstruction.

In a first aspect of the methods and devices of the present invention, the intimal layer or innermost layer of the wall of the lumen or cavity is dissected, cleaved or cut to access and expose a portion of the underlying adventitial layer or outer layer. This is accomplished with a dissection tool which is part of or disposed near the distal end of a catheter. A number of embodiments of such dissection tools are described and illustrated herein. Many of these comprise a radially expansive element configured to contact the vessel wall when in an expanded position. This feature of expansion allows the element to be introduced percutaneously in a low profile to the treatment or target site and then to expand radially to perform the treatment steps. Such expansion may be achieved by action of an inflatable member or similarly functioning device, or the element may be self-expanding.

In some cases, the expansive element comprises a cutting surface configured to cut through the intimal layer of the vessel wall to expose a portion of the underlying adventitial layer after contact with the vessel wall in the expanded position. Similarly, the expansive element may comprise an abrasive surface which is designed to abrade through the intimal layer to the underlying adventitial layer. With either surface, the surface may be rotated to aid in the dissection. Alternatively, the expansive element may have an adhesive surface adapted to adhere to an intimal layer of the vessel wall upon contact. In this case, the adhered portions of the intimal layer and attached occlusive material are peeled away from the adventitial layer when the element is removed. Such adhesion may be achieved with the use of a variety of adhesives, vacuum suction or setting the adhesive surface to various temperatures.

In other embodiments of the dissection tool, the tool comprises a radially extensible element configured to contact the vessel wall in an extended position. Typically, the element comprises a pointed instrument which is designed to cut through the intimal layer upon contact and/or by rotation of the element. In addition, an exemplary embodiment of a system of devices comprises a dissection tool and end cutter such as described in patent WO 9511633A1 and U.S. Pat. No. 5,843,102, incorporated herein by reference.

In a second aspect of the methods and devices of the present invention, the intimal layer or innermost layer of the wall of the lumen or cavity is stripped or delaminated from the underlying adventitial layer or outer layer, thereby removing the unwanted tissue. This is achieved with a stripping tool which is part of or disposed near the distal end of a catheter. Alternatively, the stripping tool is incorporated into or receivable by the catheter having the dissection tool or the dissection tool may further function as a stripping tool. A number of embodiments of such stripping tools are described and illustrated herein. The stripping tools are adapted to contact the exposed portion of the adventitial layer and advance along the exposed portion to delaminate the intimal layer from the adventitial layer along a segment of the blood vessel. The stripping tool comprises a stripping component. In some embodiments, the stripping component comprises a radially expansible ring which is positionable between the intimal and adventitial layers so that the intimal layer passes through the inside of the ring during advancement. Optionally, the delaminated material may be macerated and removed by an aspiration pump as it is stripped from the vessel. In some cases, the stripping component further comprises a funnel shaped dissection propagator which is connected to the ring to guide the delaminated material into the macerator and/or aspiration pump. Exemplary examples of maceration devices are described in related U.S. patent application Ser. No. 09/454,517, incorporated herein by reference, as well as in U.S. Provisional Application No. 06/193,539 and U.S. Provisional Application No. 60/195,653, both incorporated herein by reference. Examples of aspiration devices are described in U.S. patent application Ser. No. 09/590,915, U.S. Provisional Application No. 60/260,170, and U.S. patent application Ser. No. 09/388294, all incorporated herein by reference.

In one embodiment, the stripping component comprises a radially expansible coil positionable between the intimal and adventitial layers os that the intimal layer and attached atheroma passes through the inside of the coil during advancement. The coil may have an oblique angle formed leading edge which assists in removing material as the coil is advanced by rotation. Removed material may then be macerated and aspirated as described above.

In another embodiment, the stripping component comprises a rod having an atraumatic distal tip. The rod is angularly extendable from the catheter body and the tip is configured to be positionable between the intimal and adventitial layers. The rod is then advanced and optionally rotated to delaminate the intimal layer from the underlying adventitial layer.

In a further embodiment, the stripping component comprises an inflatable member. Here, the inflatable member is inflated in the area of dissection, previously made by a dissection tool, so that it is in contact with the exposed adventitial layer. The inflatable member is then advanced along the blood vessel, pushing and stripping the intimal layer from the adventitial layer as it progresses. To assist in providing adequate force, an anchoring component may be positioned near the area of dissection or the exposed portion of the adventitial layer and remain fixed in place during advancement of the stripping component. Fixation or anchoring of the anchoring component may be achieved by expanding the component to the extent that it overexpands the blood vessel. This will provide adequate tension for applying stripping force to the intimal layer.

In an additional embodiment, the stripping tool comprises a shaft having a proximal end and a distal end, wherein the stripping component is disposed therebetween. Further, a proximal occlusion member and a distal occlusion member are mounted on the shaft on opposite sides of the stripping component. In this way, a section of the vessel may be isolated between the occlusion members. The isolated section is fillable with saline or other solution to aide visualization by an angioscope and light source disposed between the occlusion members. Thus, the delamination process may be visualized during advancement of the stripping component.

In still a further embodiment, the stripping tool comprises a stripping component which is configured to be inserted between the intimal and adventitial layers and to be rotated around a longitudinal axis of the catheter body to delaminate the intimal layer from the adventitial layer along a segment of the blood vessel. In this case, the stripping component typically comprises a wire or stripping element which is longitudinally extended. In addition to rotation, the component may be in tension and/or a linear movement may be applied to the component to enhance separation of the internal and external vessel layers. Examples of this linear movement would be translational, vibrational, or ultrasonic motion. The stripping wire may alternatively be in tension using two percutaneous sticks that may be created by a device described in U.S. patent application Ser. No. 09/388,294, incorporated herein by reference. In tension the stripping wire may be manually pulled to remove the core, or assisted using motion to enhance separation of internal and external vessel layers, such as using sawing motion or subsonic or ultrasonic vibration as mentioned. In any case, once the component has been rotated 360 degrees, the intimal layer and associated occlusional material should be completely delaminated. The stripped material then is removed using a mechanical aspiration catheter or with a thrombectomy catheter.

In a third aspect of the present invention, dissection and stripping may be achieved simultaneously. Although both of these functions may be achieved with either a dissection tool or a stripping tool, these functions may also be achieved with combination tools. In one embodiment of a combination tool, a treatment catheter comprises a proximal occlusion member and a distal occlusion member mounted on one or more shafts so that the members may be slidably separated. Optionally, between the occlusion members may be disposed a maceration device. The catheter is inserted within a blood vessel so that the occlusion members straddle an area to be dissected and/or stripped. With the occlusion members firmly contacting the vessel walls, the occlusion members are separated to create a tension zone between them. Since the adventitial layer is more flexible than the intimal layer, the intimal layer and occlusive material will separate from the adventitial layer, wherein in may then be removed.

In a fourth aspect of the present invention, delaminated material may require cutting from the intact material for successful removal. Such cutting may be achieved with a variety of cutting tools. In a preferred embodiment, the cutting tool is comprised of a ring which slides between the intimal and adventitial layers which have been previously separated. The ring comprises a support tube and a cutting wire wherein the support tube is retractable to expose the cutting wire. The cutting wire is configured to cut through the intimal tissue when tensioned to release the delaminated intimal tissue from the vessel wall. The delaminated material may then be removed from the lumen by any suitable means.

Following any of the above described treatments, the remaining debris can be removed by activating the macerating and aspirating function of the device of the present invention as specifically described in U.S. patent application Ser. No. 09/454,517 and U.S. patent application Ser. No. 09/590,915, which claims the benefit of U.S. Provisional Application No. 60/154,752, all applications of which are incorporated herein by reference. Once the material has been removed, the dissection or stripping tools can be used to remove any remaining flaps in order to ensure complete removal within the inner diameter of the treated vessel. In addition, adjunctive procedures and devices may be performed upon the treated lesion to ensure vessel patency such as, placements of stents, stent-grafts, grafts, anti-stenotic and anti-thrombotic material, percutaneous transluminal angioplasty, radiation, and the like. Most often a stent or stent-graft will be placed to ensure that any flaps created through the dissection procedure would be tacked down.

Other objects and advantages of the present invention will become apparent from the detailed description to follow, together with the accompanying drawings.

BRIEF DESCRIPTION OF THE DRAWINGS

FIGS. 1A-1C prior art) illustrate a typical endarterectomy procedure.

FIGS. 2A-2C illustrate an embodiment of a dissection tool comprising a radially extensible pointed instrument and its method of use.

FIGS. 3A-3B illustrate a dissection tool comprising a radially expansive element and its method of cutting through an intimal layer of a blood vessel.

FIG. 4 illustrates a dissection tool comprising a radially expansive element which is expanded by an expandable member and its method of abrading through an intimal layer of the blood vessel.

FIG. 5 illustrates a dissection tool comprising a radially expansive element which is self-expanding and its method of abrading through an intimal layer of the blood vessel.

FIGS. 7A-7B illustrate a dissection tool its methods of use wherein an adhesive surface is provided by an adhesive element.

FIGS. 8A-8B depict an embodiment of a stripping tool comprising a funnel-shaped dissection propagator or stripping component and its method of use.

FIGS. 9A-9B illustrates an embodiment of a stripping tool comprising a radially expansible ring and its method of use.

FIG. 11 depicts an embodiment of a stripping tool comprising a rod having an atraumatic tip and its method of use.

FIG. 12 illustrates the stripping tool of FIG. 11 further including occlusion members to create a visualization zone.

FIG. 13 illustrates an embodiment of a stripping tool that utilizes mechanical advantage.

FIG. 14 depicts a stripping tool comprising a radially expansible coil.

FIGS. 15A-15B illustrate an embodiment of a stripping tool comprising a stripping component and an anchoring component, wherein the stripping component comprises an inflatable member, and its method of use.

FIGS. 16A-16C illustrate an embodiment of a stripping tool comprising a wire or stripping element and its method of use which includes rotating the element circumferentially to separate the intimal layer from the adventitial layer.

FIGS. 17A-17C depict an embodiment and method of use of a combination tool.

FIG. 18 illustrates an embodiment of a cutting tool.

FIGS. 19A-19E illustrate the methods of using the cutting tool of FIG. 20.

FIGS. 20A-20B depict the location of layers in a body lumen or cavity which may be treated by the methods of the present invention.

FIG. 21 illustrates a kit constructed in accordance with the principles of the present invention.

DETAILED DESCRIPTION OF THE INVENTION

Figure 6A:
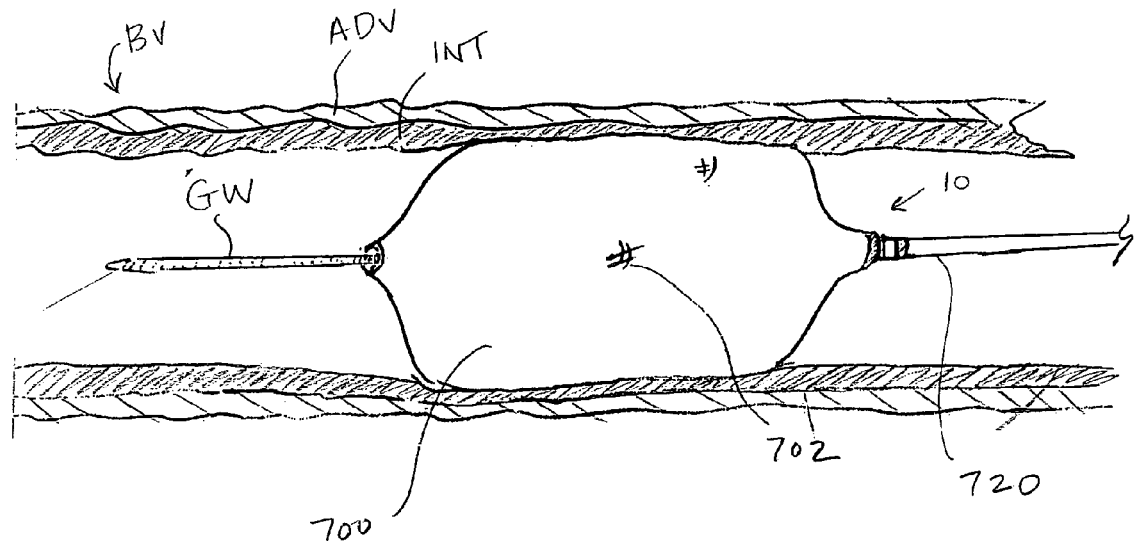
FIGS. 6A-6B depict a dissection tool comprising a radially expandable element which comprises an inflatable member having an adhesive surface and its methods of use.

Devices, systems and methods of the present invention generally relate to three basic features of an endarterectomy or similar procedure. These features include: 1) dissecting, cleaving or cutting the intimal layer or innermost layer of the wall of the lumen or cavity to access the adventitial layer or outer layer, 2) stripping or delaminating the innermost layer from the outer layer, and 3) removing the delaminated material from the lumen which may include maceration. All of these features are not essential to the present invention nor are they intended to limit the scope of the invention. However, embodiments of the present invention will be described according to these general features for clarity. Typically devices for each feature of the procedure are independent and may be used in any combination. However, some devices may be designed for specific use in combination with other devices.

I. Dissection Tools

An embodiment of a dissection tool constructed in accordance with the present invention and its method of use is illustrated in FIGS. 2A-2C. Referring to FIG. 2A, the dissection tool 10 is inserted within the lumen of the blood vessel BV to a position near the occlusion OC. As shown, the blood vessel BV has an adventitial layer ADV and an intimal layer INT to which the occlusion OC is adhered. The dissection tool 10 is part of a catheter 20 having a catheter shaft 13 with a distal tip 14. The shaft 13 has at least two lumens, one of which is a guidewire lumen 15 adapted for passage of a guidewire GW (not shown). Referring to FIG. 2B, another lumen is adapted for passage of a sharp or blunt point instrument 11 which is radially extensible such that its tip protrudes radially outward from the shaft 13. Alternatively, the instrument may be fixedly attached to the shaft 13 in this position. The instrument 11 is used to pierce, dissect, cleave or cut through the intimal layer INT to the adventitial layer ADV as shown. To assist in accessing the adventitial layer ADV, the tool 10 may additionally comprise a balloon 16 which may be inflated to force the instrument 11 against and or through the intimal layer INT. The intimal layer INT may be cut along the circumference of the lumen by rotating the shaft 13 around its axis as in the direction of the arrow. Referring now to FIG. 2C, the result is a dissection D of the intimal layer INT revealing the adventitial layer ADV underneath. As shown, the instrument 11 may be retracted and the catheter 20 withdrawn from the blood vessel BV.

Additional embodiments of the dissection tool comprise a radially expansive element configured to contact the vessel wall in an expanded position. Upon such contact, the element cuts or cleaves through the intimal layer INT to create the dissection. FIGS. 3A-3B illustrate such a treatment catheter 100 having a dissection tool and its method of use. As shown, the catheter 100 comprises a catheter shaft 106 (optionally including a mechanical aspiration pump 103), a guidewire lumen 102, an expandable member 104 mounted near its distal end 101 and a radially expansive element, in this case a cutting element 105. In use, a guidewire GW is advanced to the occlusion OC or treatment area within the blood vessel BV as shown in FIG. 3A. Once the guidewire GW is in place, the catheter 100 is advanced over the guidewire GW so that the cutting element 105 is positioned proximal to the occlusion OC at the point in which a dissection is desired. The expandable member 104 is then inflated which in turn expands the cutting element 105. The cutting element 105 has a cutting surface 108 which is pushed into the intimal layer INT as a result of the action of the expandable member 104, thereby creating a dissection. In addition, the cutting surface 108 may be configured to cut through the intimal layer INT by rotation of the radially expansive element or cutting element 105 as illustrated by the arrow. As shown in FIG. 3B, either such action creates a dissection D and exposes a portion of the adventitial layer ADV after the cutting surface 108 contacts the vessel wall in the expanded position.

FIG. 4 illustrates a similar embodiment of a treatment catheter 100 and dissection tool. Again, the catheter 100 comprises a catheter shaft 106 (optionally including a mechanical aspiration pump 103), a guidewire lumen 102, an expandable member 104 mounted near its distal end 101 and a radially expansive element, in this case a cutting element 105. Once the guidewire GW is in place, the catheter 100 is advanced over the guidewire GW so that the cutting element 105 is positioned proximal to the occlusion OC at the point in which a dissection is desired. The expandable member 104 is then inflated which in turn expands the cutting element 105. In this case, the cutting element 105 has an abrasive surface 115 which is configured to abrade through the intimal layer INT to expose a portion of the adventitial layer ADV. Typically, such abrasion is achieved by rotation of the radially expansive cutting element 105 as indicated by the arrow.

In any of the above embodiments, the radially expansive element may be self-expanding such that an expandable member 104, such as a balloon, is not required to expand the element. In these cases, the radially expansive element may be constructed of a self-expanding material, such as shape-memory alloy or nickel titanium. Expansion may be activated by release of any restriction holding the element a collapsed form. FIG. 5 illustrates a dissection tool or treatment catheter 100 having a radially expansive element 117 which is self-expanding. Again, the catheter 100 comprises a catheter shaft 106, a guidewire lumen 102, and the radially expansive element 117 disposed near its distal end 101. Once the guidewire GW is in place, the catheter 100 is advanced over the guidewire GW so that the element 117 is positioned proximal to the occlusion OC at the point in which a dissection is desired. The element 117 is then expanded, as shown, so that it contacts the walls of the blood vessel BV. In this case, the element 117 has an abrasive surface 115 which is configured to abrade through the intimal layer INT create a dissection D and expose a portion of the adventitial layer ADV. Typically, such abrasion is achieved by rotation of the radially expansive cutting element 105 as indicated by the arrow.

Figure 6B:
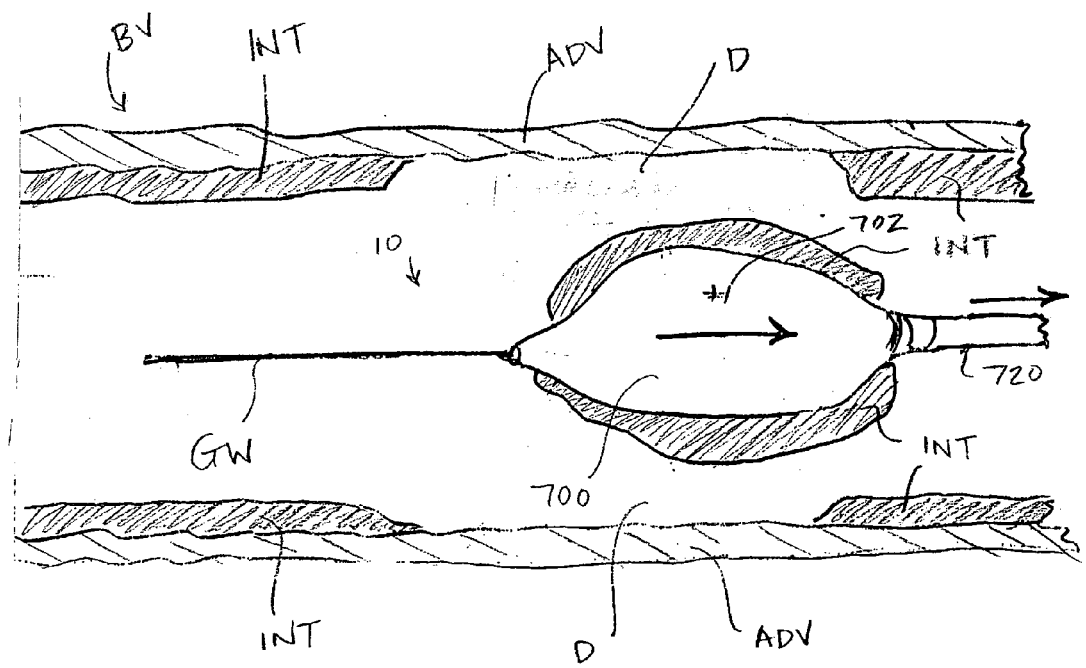

In additional embodiments of the dissection tool, the radially expandable element has an adhesive surface adapted to adhere to an intimal layer of the vessel wall upon contact with the vessel wall in the expanded position. In one such embodiment, shown in FIG. 6A, the radially expandable element comprises an inflatable member 700 having an adhesive surface 702. The adhesive surface 702 may comprise cyanoacrylate, UV curable adhesive, epoxy, bioadhesives, collagen based adhesive for biological applications and other adhesive materials. Further, the adhesive surface 702 may comprise a material having a temperature in the range of approximately −100° C. to 0° C. This may be achieved by inflating the member 700 with a liquid having a temperature in a similar range. Alternatively, the adhesive may comprise a material having a temperature in the range of approximately 42° C. to 100° C. Again, this may be achieved by inflating the member 700 with a liquid having a temperature in a similar range. The inflatable member 700 is mounted on the distal end of a shaft 720 through which a guidewire GW may be placed. Once the tool 10 is positioned within the blood vessel BV in a desired location, the member 700 is inflated so that the adhesive surface 702 contacts the intimal layer INT or material to be removed from the lumen. As shown in FIG. 6B, once the adhesive surface 702 has adhered to the intimal layer INT or material, the member 700 is deflated. Upon deflation, the member 700 removes the adhered portions from the vessel wall to create a dissection D and expose portions of the adventitial layer ADV. The tool 10 may then be withdrawn as indicated by arrows.

It may be appreciated that such an adhesive surface may be used with previously described embodiments of the expansive element. For example, an adhesive surface may replace the cutting surface in FIGS. 3A-3B or the abrasive surface in FIGS. 4-5 and function in a manner similar to that described above. Further, as shown in FIGS. 7A-7B, an adhesive surface 800 may be provided by an adhesive element 802 which is part of a dissection tool 10. Here, the adhesive element 802 is disposed on the distal end of a shaft 804. To create a dissection, the adhesive element 802 is positioned so that the adhesive surface 800 contacts the vessel wall and adheres to the intimal layer INT of the blood vessel BV. Upon withdrawal of the adhesive element 802, shown in FIG. 7B, the adhered portions of the intimal layer INT are removed to expose portions of the adventitial layer ADV. In this and other cases mentioned above, the adhesive surface 702 may comprise vacuum suction, any of the adhesive materials described above, or any suitable material.

Angioscopy and IVUS can be used with any of the dissection tools 10 to visualize the dissection.

II. Stripping Tools

The next feature of the present invention involves stripping or delaminating the innermost layer or intimal layer from the outer layer or adventitial layer. Generally, once a dissection of the intimal layer has been made to expose a portion of the adventitial layer, the intimal layer may be delaminated from the adventitial layer with the use of a variety of stripping tools.

In one embodiment, shown in FIG. 8A, the stripping tool 20 comprises a shaft 24 and a funnel-shaped dissection propagator or stripping component 22. The component 22 is configured to contact the exposed portion of the adventitial layer ADV in the area of the dissection D. Alternatively, the component 22 may be attached to a ring 25 which contacts the adventitial layer ADV in the same manner. The ring 25 is typically a radially expansible ring which expands to fit any sized lumen. As shown in FIG. 8B, the component 22 is advanced toward the occlusion OC so that the dissected intimal layer INT is delaminated from the adventitial layer ADV and drawn into the funnel-shaped component 22. Such action may be assisted by a mechanical aspiration pump 17 within the shaft 24. In addition, a rotating macerator 18 may be incorporated in the aspiration pump 17 to facilitate maceration and removal of the occlusive material OC and delaminate intimal layer INT. The aspiration pump 17 and macerator 18 are rotated using a variable speed motor drive unit. The motor drive unit may also be put in reverse to change the direction of the pump 17 and macerator 18. When such a pump 17 and macerator 18 are present during the initial creation of the dissection, these devices may be utilized during the dissection step to ensure complete aspiration of the occlusive material and potential emboli. In addition, a separate pump and macerator may also be positioned on the distal side of the occlusion OC for added protection against loose material becoming embolic.

In a similar embodiment, illustrated in FIGS. 9A-9B, the stripping tool 20 may comprise a radially expansible ring 110 which is also positionable between the intimal layer INT and adventitial layer ADV of the blood vessel BV. Here, the ring 110 is mounted on a shaft 111 which may be extensible from a treatment catheter (not shown) or may be independently insertable into the blood vessel BV. As shown in FIG. 9A, an expansion member 112 may be inserted through the ring 110 to provide a number of functions. The expansion member 112 may first be used to expand a cutting element 105, as previously shown and described in FIGS. 3A-3B. As described, the cutting element 105 has a cutting surface 108 which is pushed into the intimal layer INT as a result of the action of the expandable member 104/expansion member 112, thereby creating a dissection D and exposing a portion of the adventitial layer ADV. Referring now to FIG. 9A, the expansion member 112 may then be used to expand the ring 110 from a reduced dimension (shown in dashed line) to an expanded dimension. The expansion member 112 may also be used as a guide for directing the ring 110 into the dissection D and between the intimal layer INT and adventitial layer ADV, as shown. Referring to FIG. 9B, the ring 110 is advanced, or retracted depending on the direction of its insertion, along the adventitial layer ADV of the blood vessel BV so that the intimal layer INT and associated occlusive material OC are delaminated and pass through the inside of the ring 110. The delaminated material may be drawn into a mechanical aspiration catheter 120 which houses an aspiration pump 103 and optionally a macerator, therein described by U.S. Provisional Application No. 60/260,170, U.S. patent application Ser. No. 09/454,517, and U.S. patent application Ser. No. 09/590,915 which claims the benefit of U.S. Provisional Application No. 60/154,752.

It may be appreciated that although the radially expansible ring 110 has been described as a separate tool, a stripping tool, from the cutting element 105, a dissection tool, the ring 110 may serve both purposes. The ring 110 may have a cutting surface 108 or any other type of surface suitable for dissection wherein the ring 10 is used for dissection. The ring 110 may then be used in a manner described above for stripping or delaminating the intimal layer INT from the adventitial layer ADV.

Figure 10A:
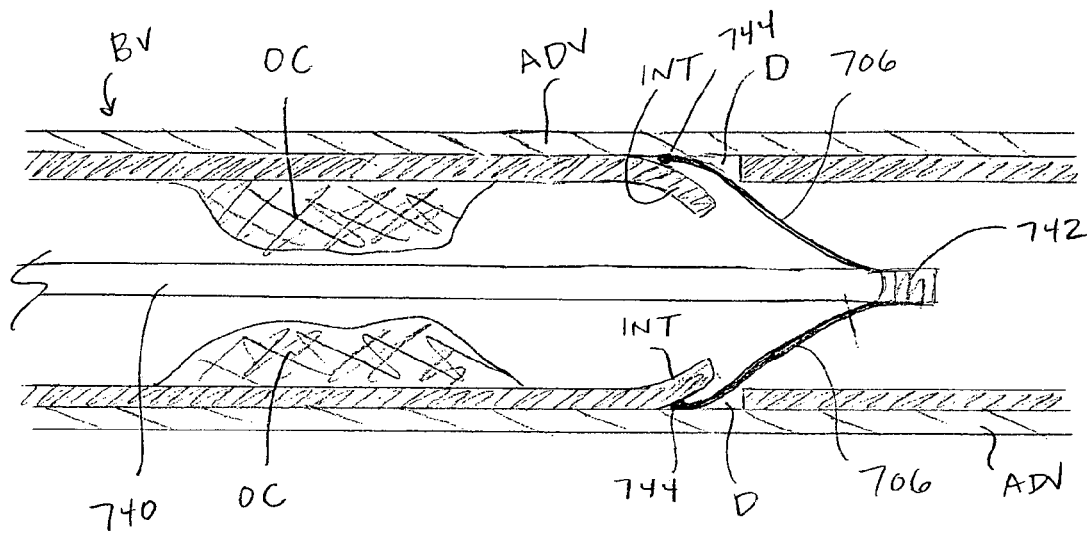
FIGS. 10A-10B illustrate an embodiment of a stripping tool comprising radially expandable arms which are positionable between the intimal and adventitial layers and its method of use.
Figure 10B:
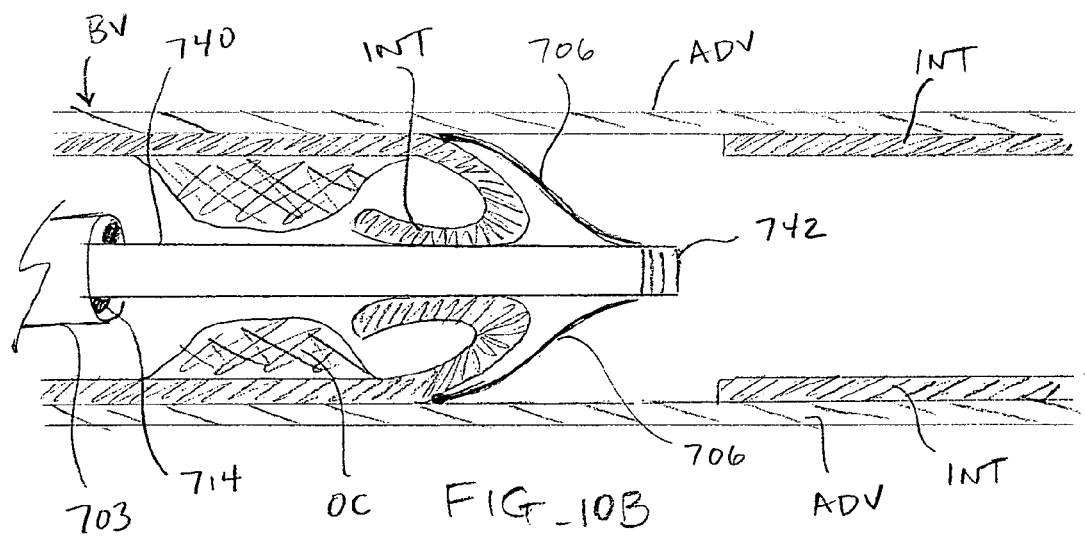

FIGS. 10A-10B illustrate an additional embodiment of a stripping tool and its methods of use. Referring to FIG. 10A, the stripping tool 700 comprises a shaft 740 having a distal end 742 whereupon at least one but typically two or more radially expandable arms 706 are mounted. The arms 706 are expandable so that blunt-end tips 744 of the arms 706 are positionable between the intimal layer INT and adventitial layer ADV in the area of dissection D. Referring to FIG. 10B, the stripping tool 700 is then retracted or moved axially so that the tips 744 slide along the exposed adventitial layer ADV creating a dissection plane or delamination of the intimal layer INT from the adventitial layer ADV. As shown, the delaminated intimal layer TNT collects within the arms 706 along with associated thrombus, atheroma or occlusive material OC. The removed material may be directed towards a mechanical cutting or aspiration system 714 where it is cut and removed. The system 714 may be disposed in a catheter shaft 703 of a treatment catheter 701 or it may be disposed in a separate catheter or device.

Referring to FIG. 11, an additional embodiment of a stripping tool and its methods of use is shown. Here, the stripping tool 20 includes a shaft 510 having a guidewire lumen 505 therethrough and a stripping component 500 comprising a rod 502 having an atraumatic distal tip 504. Once the stripping tool 20 is positioned in the blood vessel BV near the dissection area D, by advancement over the guidewire GW, the rod 502 is angularly extended from the shaft 510 so that the tip 504 is positioned in the dissection area D between the intimal layer INT and the adventitial layer ADV, as shown. The rod 502 may be adjusted angularly or extendably to accommodate blood vessels of various sizes. By advancing the tool 20 so that the rod 502 moves along the exposed adventitial layer ADV, the intimal layer INT is delaminated and a cleavage plane is created. In addition, the rod 502 may be rotated around a longitudinal axis 508 of the shaft 510, as indicated by the arrow, to assist in the cleaving process.

Referring to FIG. 12, the above described embodiment of the stripping tool 20 may optionally include devices for visualization of the cleaving process. Here, a light source and angioscope 520 are disposed on the shaft 510 near the stripping component 500. A proximal occlusion member 512 is shown mounted on the shaft 510 and a distal occlusion member 514 is shown mounted on a separate shaft 516 which is introduced through a lumen in the shaft 510. However, it may be appreciated that the distal occlusion member 514 may be mounted on shaft 510 in other embodiments. Once the blood vessel BV is occluded by the occlusion members 512, 514, the portion of the blood vessel therebetween may be filled with saline SA or other suitable fluid to form a zone for visualization. Since the stripping component 500 is located in this zone, the stripping or cleaving process can be monitored through visualization. Such monitoring may be achieved continuously throughout the cleaving process or at discrete intervals.

Another embodiment of a stripping tool is shown in FIG. 13. Here, the stripping tool 400, comprising a shaft 402, having distal end 404, a proximal end and a threaded surface 406 along at least a portion of its length, may be inserted into the blood vessel BV. In this embodiment, a stripping component 408 is mounted on the shaft 402 in a locked position. The stripping component 408 is then positioned against the exposed portion of the adventitial layer ADV. The shaft 402 may then be rotated which advances the stripping component 408 between the intimal layer INT and adventitial layer ADV to create a cleavage plane CP. It may be appreciated that the component 408 may be retracted by reverse rotation of the shaft 402. In any case, rotation may be provided by a torque provider which may attach to the proximal end of the shaft 402. In addition, the stripping tool 400 may also include means for locking the stripping component 408 to the shaft 408, typically by interlocking the threaded surface 406 with threads on the stripping component 408. This may terminate the stripping after a specified distance.

Yet another embodiment of a stripping tool is depicted in FIG. 14. As shown, the stripping tool 450 comprises a shaft 451, allowing the passage of a guidewire GW therethrough, and stripping component 452, comprising a radially expansible coil 454. The coil 454 may have an oblique angle formed leading edge 456, as shown. When the stripping component 452 is positioned near the dissection area D, the coil 454 may be expanded so that the leading edge 456 is in contact with an exposed portion of the adventitial layer ADV. Such positioning will allow the edge 456 to move between the intimal layer INT and adventitial layer ADV when the tool 450 is advanced. Advancement of the tool 450 is achieved by rotation, as indicated by arrows, of the coil 454 by a drive unit or other means. As the intimal layer INT is delaminated, a cleavage plane is created and the stripped material, including associated thrombus and occlusive material OC, is passed through the inside of the coil 454. The stripped material is then removed, typically by maceration and aspiration.

FIGS. 15A-15B illustrate an additional embodiment of a stripping tool 601 and its methods of use. As shown in FIG. 15A, the stripping tool 601 comprises an anchoring component 606 mounted on a shaft 605 and a stripping component 600 mounted on a separate shaft 607. The shafts 605, 607 are coaxially arranged so that shaft 605 is slidably disposed within shaft 607. The stripping tool 601 is positioned within the blood vessel BV so that the anchoring component 606 is positioned near the previously created dissection D where a portion of the adventitial layer ADV is exposed. The anchoring component 606 is then expanded so that it firmly contacts the vessel wall. Here the component 606 is inflatable so the component 606 may be overinflated, as shown, expanding the blood vessel BV to ensure anchoring ability. The stripping component 600 is positioned within the area of dissection D. Here the component 600 comprises an inflatable member 602 which is inflated so that it contacts a portion of the exposed adventitial layer ADV. Referring to FIG. 15B, the inflatable member 602 is then advanced along the blood vessel, or in this case retracted toward the proximal end of the tool 601, to create a cleavage plane. Optionally, the inflatable member 602 may house an angioscope 604 for visualization of the cleaving process. As the member 602 moves along the exposed adventitial layer ADV, the intimal layer INT is delaminated and pushed along by the member 602. Since such pushing may require significant force, the anchoring component 606 will assist in creating tension. The stripping component 600 may also include surface features to enhance removal of the intimal layer INT such as those previously described in relation to FIGS. 6A-6B and FIGS. 7A-7B. The delaminated material and associated occlusive material OC is then removed, typically by maceration and aspiration.

FIGS. 16A-16C illustrate an additional embodiment of a stripping tool for use in longitudinal vessel stripping. In this concept a wire or stripping element 201 is used to delaminate the intimal layer INT from the adventitial layer ADV of a blood vessel BV. Generally, a portion of the adventitial layer ADV is first exposed by any suitable dissection method. As shown in a cross-sectional view in FIG. 16A, the distal end 202 of the stripping element 201 is then inserted into the dissection D and wedged between the intimal layer INT and adventitial layer ADV. The element 201 is then advanced longitudinally along the blood vessel BV between the two layers INT, ADV. Such advancement is illustrated in FIG. 16B where one portion of the illustration is a cross-sectional view and another is a perspective view to illustrate the positioning of the element 201. Referring to FIG. 16C, the stripping element 201 is then rotated around the vessel circumferential plane, in the direction of the arrows, to loosen and delaminate the intimal layer INT from the adventitial layer ADV. The intimal layer INT is shown separated the from the adventitial layer ADV. The stripping element 201 may be in tension and/or a linear movement may be applied to the element 201 to enhance separation of the internal and external vessel layers. Examples of this linear movement would be translational, vibrational, or ultrasonic motion. Once the element 201 has been rotated 360 degrees, the intimal layer INT should be completely delaminated.

III. Combination Tools

Although each of the above described dissection tools and stripping tools may be used with each other, some tools may provide both dissection and stripping functions. This was previously mentioned above in relation to the radially expansible ring 110 in FIGS. 9A-9B. An additional example of an embodiment providing a combination of functions is illustrated in FIGS. 17A-17C along with its method of use.

FIG. 17A illustrates a treatment catheter 651 comprising a proximal occlusion member 650 mounted on a shaft 653 and a distal occlusion member 652 mounted on a separate shaft 658. The shafts are coaxially arranged so that shaft 658 is slidably disposed within shaft 653. In addition, a maceration device 660 may be disposed between the members 650, 652 as shown. The catheter 651 is inserted within a blood vessel BV and positioned so that the occlusion members 650, 652 are disposed on opposite sides of an area which is desired to be dissected and/or stripped. Such positioning may be achieved with the use of a guidewire GW, as shown. In this example, the occlusion members 650, 652 are positioned on opposite sides of an occlusion OC and inflated so that they firmly contact the intimal layer INT. Referring to FIG. 17B, the catheter shaft 658 is then elongated between the occlusion members 650, 652, by slidably advancing the shaft 658 out from the coaxial shaft 653, which moves the occlusion members 650, 652 apart. Thus, a tension zone is created between the members 650, 652. Since the adventitial layer ADV is more flexible than the intimal layer INT, the intimal layer TNT and any associated occlusive material OC will separate from the adventitial layer ADV. A cleavage plane CP is shown where the intimal layer INT has delaminated from the adventitial layer ADV. In addition, the intimal layer INT may split or crack exposing the adventitial layer ADV and creating fragments of loose tissue and occlusion material, as depicted in FIG. 17C. The delaminated material may then be macerated by the maceration device 660, shown positioned between the occlusion members 650, 652, or any other suitable device.

It may be appreciated that the above described embodiment may be used for dissection and stripping of an area, as described, or it may be used to simply create a dissection. In the latter case, the occlusion members 650, 652 may be positioned relatively close together on opposite sides of an area in which a dissection is desired to be made. Separation of the members 650, 652 may simply split open the intimal layer INT between the members 650, 652 creating dissection. The catheter 651 may then be removed and an area may be stripped using the dissection as an entry point by any desired method. In addition, the occlusion members 650, 652 may both be mounted on the same shaft wherein the members are separated by extension of the shaft.

IV. Cutting Tools

The last of the three basic features mentioned of an endarterectomy or similar procedure includes removing the delaminated material from the lumen. Removal may occur during or after the stripping process. For example, the material may be gradually aspirated and/or macerated as it is delaminated to remove it from the body lumen. Or, the material may first be delaminated and then separately removed. In some cases, the delaminated material is present in discrete chunks or sections which are easily removed by aspiration and/or maceration. In other cases, it is necessary to cut the delaminated material from the intact material within the blood vessel to allow removal. Cutting may be achieved with a variety of cutting tools. In addition, cutting may also be achieved with any of the previously described dissection tools.

An embodiment of a cutting tool is illustrated in FIG. 18 and its method of use is depicted in FIGS. 19A-19E. As depicted in FIG. 18, the cutting tool 300 is comprised of a support tube 301, a cutting wire 302, a shaft 303, a distal end 304, a handle 307, a lever 306 to control the cutting wire 302, and a lever 305 to retract the support tube 301. The support tube 301 may be comprised of any suitable material, such as nitinol or spring steel hypotube, and forms a loop near the distal end 304 as shown. Within the tube 301 resides the cutting wire 302 shown in dashed line; the wire 302 may be comprised of any suitable material such as nitinol or spring steel wire. The tool 300 is illustrated in use in FIGS. 19A-19E. Referring to FIG. 19A, the cutting tool 300 is inserted within a blood vessel BV wherein a portion the intimal layer INT has been delaminated from the adventitial layer ADV creating a core C and a cleavage plane CP therebetween. The tube 301 is retracted within the shaft 303 as shown. Referring to FIG. 19B, support tube 301 and cutting wire 302 loop is then placed over the core C so the core C passes through the loop. As depicted in FIG. 19C, the support tube 301 and cutting wire 302 loop is then advanced through the cleavage plane CP to a desired position wherein the core C will be cut. As shown in FIG. 19D, the support tube 301 is retracted by manipulating lever 305 to expose the cutting wire 302. The support tube 301 is pulled back into the shaft 303 so the cutting wire 302 remains surrounding the core C. Referring to FIG. 19E, the cutting wire 302 is then pulled/tensioned to cut through the intimal layers INT and the core C by manipulating lever 306. This releases the delaminated material from the intact material within the blood vessel BV. The delaminated material may then be removed from the lumen by any suitable means.

Contrast may be injected through the cutting tool in order to facilitate visualization.

V. Adjunctive Therapies

Depending on the occlusion to be treated, a distal protection device, such as a balloon fixed to a guidewire, or a filter device, may be employed distal of the occlusion and expanded to minimize any embolization of clot or other material. In addition an occlusion balloon may be deployed distally of the occlusion and one proximal of the occlusion to isolate the lesion and allow the treatment device to infuse:

Thrombolytic Agents (Enzymatic action breaks down fibrin clot matrix.)
    Alteplase, tPA, Activase®, Genentech, Inc.
    Anistrpelase, a-SK, Eminase®, Roberts Pharmaceuticals
    Reteplase, r-PA, Retavase®, Centocor, Inc.
    Streptokinase, SK, Streptase®, AstraZeneca, Inc.
    Tenecteplase, TNK, TNKase®, Genentec, Inc.
    Abbokinase®, Abbott, Inc. (not currently marketed)

GP IIb/IIIa Inhibitors (Inhibit fibrinogen binding site of platelet membrane.)
    Abciximab, ReoPro®, Centecor, Inc.
    Tirofiban, Aggrastat®, Merck, Inc.
    Eptifibatide, Integrelin®, Cor Therapeutics, Inc.
    Other IIb/IIIa Inhibitors: Bitistatin, Kistrin
    Other anti-platelet agents: Aspirin Anti-Thrombin Agents and Agents Directed toward Prevention of Restenosis
    Heparin (LMW contains most anticoagulant activity, also inhibits smooth muscle Proliferation and migration, examples include enoxaparine (Lovenox®), dalteparin (Fragmin®) and ardeparin (Normoflo®))
    Other anti-thrombin agents: Hirudin, Argatronban, PPACK (inhibit thrombin induced platelet activation and platelet secretion of PDGF which is responsible for smooth muscle proliferation and migration.)
    Radioactive agents (vascular brachytherapy, inhibits smooth muscle proliferation)
    Locally delivered nitrate (nitric oxide, prevents reflex vasoconstriction at site of injury and inhibits activation of circulating platelets in order to decrease late luminal narrowing)
    HA11077 (Inhibits action of cellular protein kinases and sequestration of cellular calcium, acts as vasodilator. Shown to inhibit smooth muscle proliferation.)
    Other anti-restenosis agents: calcium antagonists, angiotensin converting enzyme inhibitor, anti-inflammatory agents, steroidal agents, anti-mitotic agents, HMG CoA reductase inhibitors, colchicine, angiopeptin, cytoclasin B Gene Therapeutic Agents
    Agents are currently under development in hopes of preventing restenosis and promoting angiogenesis. Agents may be delivered via plasmid vectors or by viral vectors. Examples include genes relating to: VEGF, C-myb, FGF, transforming growth factor b, endothelial growth factor, protooncogenes such as C-myc, C-myg, CDC-2, PCNA.

Chemotherapeutic Agents

Agents designed to treat malignancies. Examples might include adriamycin (Doxorubicin®).

Imaging Media

Contrast media, radioactively labeled agents.

Other Potential Agents

Plasminogen additive as an adjunct to thrombolytic therapy, immunosuppressive agents.

In addition, saline, pharmacologic agents such as tPA, ReoPro, platelet aggregation inhibitors and the like, or chemical ablation agents or acid solutions such as those described in PCT Application No. PCT/US99/15918 (WO 00/03651) may be used.

VI. In General

It may be appreciated that the above described devices and methods may be adapted for use in other body lumens and cavities, such as the esophagus, stomach, lungs, kidneys, intestines, rectum and uterus, to name a few. In these and other cases, a first layer may be dissected and stripped from a second layer of the lumen or cavity wall. FIG. 20A illustrates the location of a first layer or inner layer 900 and a second layer or outer layer 902 of a body lumen 904. As shown, the inner layer 900 substantially covers the outer layer 902 in the lumen. FIG. 20B illustrates the location of a first layer or inner layer 900 and a second layer or outer layer 902 of a body cavity 906. Again, the inner layer 900 substantially covers the outer layer 902 in the lumen. In either case, the inner layer 900 may not cover the outer layer 902 throughout the lumen 904 or cavity 906, but may only cover the outer layer 902 in the target location or specific area to be treated. Although illustrated separately, in many embodiments the terms lumen and cavity may be used synonymously. In addition to the inner layer, various tissues, tumors or other material may be removed in a similar fashion. The above described devices and methods may also be used in the vascular system for procedures other than endarterectomies and may be used to create cleavage planes between tissues, layers and other materials other than the intimal and adventitial layers of the vessel wall.

Referring now to FIG. 21, kits 1000 according to the present invention comprise any of the above described devices related to percutaneous endarterectomy or similar procedures and instructions for use IFU. For example, kits 1000 may include a dissection tool 1010 and instructions for using the dissection tool according to the methods of the present invention. Typically the dissection tool 1010 is disposed near the distal end of a percutaneous catheter 1012. Alternatively or in addition, the kits 1000 may include a stripping tool 1014 and/or a cutting tool 1016 and instructions for use. Optionally, the kits may further include any of the other components described above, such as a guidewire GW, aspiration pump 1018, macerator 1020, various percutaneous treatment catheters and other components. Further, the kits 1000 may include an adhesive material 1030 for application to an adhesive surface which is typically located on a dissection tool 1010. All kit components will usually be packaged together in a pouch 1032 or other conventional medical device packaging. Usually, those kit components which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

While the above is a complete description of the preferred embodiments of the invention, various alternatives, modifications, and equivalents may be used. Therefore, the above description should not be taken as limiting the scope of the present invention.

What is claimed is:

1. A device for percutaneously exposing an outer layer of a body lumen or body cavity of a patient which is covered by an inner layer of the body lumen or body cavity comprising:
   a catheter body having a proximal end, a distal end and a lumen therethrough; and
   a dissection tool disposed near the distal end of the catheter body, the dissection tool comprising a radially expansive element circumferentially surrounding the catheter body and a cutting surface extending circumferentially about the radially expansive element, the cutting surface having a continuous cutting edge positioned radially outwardly from the radially expansive element by a preselected distance so that the cutting surface traverses the inner layer to the outer layer without penetrating the outer layer upon expansion of the element.

2. A device as in claim 1, wherein the body lumen comprises a blood vessel, the inner layer comprises an intimal layer, and the outer layer comprises an adventitial layer, and wherein the catheter body is sized to be positioned within the blood vessel and the cutting surface is positioned a distance radially outwardly from the radially expansive element so that the cutting surface traverses the intimal layer to the adventitial layer without penetrating the adventitial layer upon expansion of the element.

3. A device as in claim 2, wherein the dissection tool includes a mechanism which rotates the cutting surface.

4. A device as in claim 2, wherein the dissection tool includes a mechanism which advances the radially expansive element along a portion of the adventitial layer to delaminate the intimal layer from the adventitial layer along a segment of the blood vessel.

5. A device as in claim 2, wherein the dissection tool further includes an inflatable member surrounded by the radially expansive element so that the element is expandable by action of the inflatable member.

6. A device as in claim 2, further comprising a stripping tool adapted to be received within the catheter body lumen, said stripping tool comprising a stripping component configured to contact the exposed portion of the adventitial layer and advance along the exposed portion to delaminate the intimal layer from the adventitial layer along a segment of the blood vessel.

7. A device as in claim 6, wherein the stripping tool further comprises a shaft having a proximal end, a distal end and a threaded surface along at least a portion of its length, wherein the stripping component is mounted on the shaft so that rotation of the shaft advances the stripping component along the shaft.

8. A device as in claim 7, wherein the stripping component is mounted on the shaft so that rotation of the shaft linearly advances the stripping component along the shaft without rotating the stripping component.

9. A device as in claim 6, wherein the stripping component comprises a radially expansible ring positionable between the intimal and adventitial layers so that the intimal layer passes through the inside of the ring during advancement.

10. A device as in claim 9, wherein the catheter further comprises an aspiration lumen and the stripping component further comprises a funnel shaped dissection propagator connected to the ring to guide the delaminated intimal layer into the aspiration lumen.

11. A device as in claim 10, wherein the catheter further comprises a macerating element within the aspiration lumen and/or dissection propagator to macerate the delaminated intimal layer.

12. A device as in claim 6, wherein the stripping component comprises at least one radially expandable arm having a blunt-end tip configured to be positionable between the intimal and adventitial layers so that the intimal layer is delaminated as the stripping component is retracted.

13. A device as in claim 6, wherein the stripping component comprises a radially expansible coil positionable between the intimal and adventitial layers so that the intimal layer passes through the inside of the coil during advancement.

14. A device as in claim 13, wherein the coil has an oblique angle formed leading edge and the coil is advanceable by rotation.

15. A device as in claim 6, further comprising a mechanical pump adapted to be received within the catheter body lumen.

16. A device as in claim 15, further comprising a macerating element located at least partially along the length of said mechanical pump.

17. A device as in claim 6, wherein the stripping component comprises a rod having an atraumatic distal tip, the rod being angularly extendable from the catheter body and the tip being configured to be positionable between the intimal and adventitial layers.

18. A device as in claim 17, wherein the rod is rotatable around a longitudinal axis of the catheter body.

19. A device as in claim 17, wherein the rod is angularly and/or extendably adjustable.

20. A device as in claim 6, wherein the stripping component comprises an inflatable member.

21. A device as in claim 20, wherein the stripping component further comprises an angioscope disposed within the inflatable member for visualization of the delamination process.

22. A device as in claim 20, wherein the stripping tool further comprises an anchoring component configured to contact the vessel wall near the exposed portion of the adventitial layer and remain fixed in place during advancement of the stripping component.

23. A device as in claim 22, wherein the anchoring component comprises an inflatable member configured to over-expand the blood vessel.

24. A device as in claim 6, wherein the stripping tool further comprises:
a shaft having a proximal end and a distal end, wherein the stripping component is disposed therebetween;
a proximal occlusion member mounted on the shaft proximal to the stripping component;
a distal occlusion member mounted on the shaft distal to the stripping component; and
an angioscope and light source disposed between the occlusion members,
wherein the occlusion members are capable of isolating a section of the vessel that is fillable with saline for visualization of the delamination by the angioscope during advancement of the stripping component.

25. A device as in claim 2, further comprising a stripping tool adapted to be received within the catheter body lumen, said stripping tool comprising a stripping component configured to be inserted between the intimal and adventitial layers and to be rotated around a longitudinal axis of the catheter body to delaminate the intimal layer from the adventitial layer along a segment of the blood vessel.

26. A device as in claim 2, further comprising a cutting tool adapted to be received within the catheter body lumen, said cutting tool comprising a ring configured to be advanceable along a cleavage plane between a delaminated intimal layer and the adventitial layer.

27. A device as in claim 26, wherein the ring comprises a support tube and a cutting wire, wherein the support tube is retractable to expose the cutting wire which is configured to cut through the delaminated intimal layer when tensioned.

28. A device as in claim 1, wherein the radially expansive element is self-expandable.

29. A device as in claim 1, further comprising an aspiration pump disposed within the catheter body.

30. A device as in claim 29, further comprising a macerator.

31. A device as in claim 1, wherein the catheter body further includes a guidewire lumen extending between the proximal and distal ends.

32. A device for percutaneously exposing an outer layer of a body lumen or body cavity of a patient which is covered by an inner layer of the body lumen or body cavity comprising:
a catheter body having a proximal end, a distal end, and a lumen therethrough;
said catheter body further includes a radially expansive element circumferentially surrounding the catheter body; and
a dissection means including a blade having a continuous cutting edge positioned radially outwardly from the radially expansive element for traversing the inner layer to the outer layer along a circumference of the body lumen or body cavity, without penetrating the outer layer to expose a portion of the outer layer, by expanding said blade.

33. A device as in claim 32, further comprising a stripping means adapted to be received within the catheter body lumen for delaminating the inner layer from the outer layer.

34. A device as in claim 33, further comprising a cutting means adapted to be received within the catheter body for cutting through and releasing the delaminated inner layer.

35. A system for percutaneously treating a body lumen or body cavity of a patient comprising:
a dissection catheter having a proximal end, a distal end, a catheter body, and a dissection means comprising a radially expansive element circumferentially surrounding the catheter body and a cutting surface extending circumferentially about the radially expansive element, the cutting surface having a continuous cutting edge positioned radially outwardly from the radially expansive element for dissecting an inner layer of the body lumen or body cavity to expose a portion of an outer layer of the body lumen or body cavity and
a stripping catheter having a proximal end, a distal end, and a stripping means disposed near its distal end to advance along the exposed portion of the outer layer for delaminating the inner layer from the outer layer.

36. A system as in claim 35, further comprising a cutting catheter having a proximal end, a distal end, and a cutting means disposed near its distal end for cutting through the delaminated inner layer for removal.

37. A system for percutaneously treating an occlusion in a blood vessel of a patient comprising:
a dissection catheter having a proximal end, a distal end, a catheter body, and a dissection tool comprising a radially expansive element circumferentially surrounding the catheter body and a cutting surface extending circumferentially about the radially expansive element, the cutting surface having a continuous cutting edge positioned radially outwardly from the radially expansive element adapted to expose a portion of an adventitial layer; and a stripping catheter having a proximal end, a distal end and a stripping tool disposed near the distal end adapted to contact the exposed portion of the adventitial layer and advance along the exposed portion to delaminate the intimal layer from the adventitial layer along a segment of the blood vessel.

38. A system as in claim 37, wherein the stripping tool comprises a stripping component comprising a radially expansible ring positionable between the intimal and adventitial layers so that the intimal layer passes through the inside of the ring during advancement.

39. A system as in claim 37, wherein the stripping catheter further comprises body lumen and a mechanical pump adapted to be received within the body lumen.

40. A system as in claim 39, further comprising a macerating element located at least partially along the length of the mechanical pump.

* * * * *